United States Patent
Schwammenthal et al.

(10) Patent No.: US 11,648,391 B2
(45) Date of Patent: May 16, 2023

(54) BLOOD PUMP

(71) Applicant: Magenta Medical Ltd., Kadima (IL)

(72) Inventors: Ehud Schwammenthal, Ra'anana (IL); Yosi Tuval, Even Yehuda (IL); Daniel Glozman, Kfar Yona (IL)

(73) Assignee: Magenta Medical Ltd., Kadima (IL)

( * ) Notice: Subject to any disclaimer, the term of this patent is extended or adjusted under 35 U.S.C. 154(b) by 387 days.

(21) Appl. No.: 16/859,492

(22) Filed: Apr. 27, 2020

(65) Prior Publication Data
US 2020/0254162 A1    Aug. 13, 2020

Related U.S. Application Data

(63) Continuation of application No. 15/888,771, filed on Feb. 5, 2018, now Pat. No. 11,484,701, which is a (Continued)

(51) Int. Cl.
*A61M 60/135* (2021.01)
*A61M 60/857* (2021.01)
(Continued)

(52) U.S. Cl.
CPC ..... *A61M 60/833* (2021.01); *A61B 17/12136* (2013.01); *A61B 17/12168* (2013.01); (Continued)

(58) Field of Classification Search
CPC .............. A61M 60/833; A61M 60/135; A61M 60/216; A61M 60/857; A61M 2205/505; (Continued)

(56) References Cited

U.S. PATENT DOCUMENTS 4,822,345 A    4/1989  Danforth
4,886,506 A   12/1989  Lovgren et al.
(Continued)

FOREIGN PATENT DOCUMENTS

AU    2013205145 A1    5/2013
AU    2013257469 B2    3/2016
(Continued)

OTHER PUBLICATIONS

Advisory Action for U.S. Appl. No. 15/888,771 dated May 4, 2022.
(Continued)

*Primary Examiner* — Joseph M Dietrich
*Assistant Examiner* — Michael T. Holtzclaw
(74) *Attorney, Agent, or Firm* — Dorsey & Whitney LLP

(57) ABSTRACT

Apparatus and methods are described including a blood pump that includes a catheter, a first impeller disposed on the catheter, and a second impeller disposed on the catheter, proximally to the first impeller. A control unit drives the first and second impellers to pump blood of a subject, by driving the first and second impellers to rotate. The blood pumps is configured such that (a) the first and second impellers are shaped differently from each other when the first and second impellers are in non-radially-constrained configurations, (b) the first and second impellers are sized differently from each other when the first and second impellers are in non-radially-constrained configurations, and/or (c) the first and second impellers are driven by the control unit to rotate under respective rotation conditions that are different from each other. Other applications are also described.

6 Claims, 9 Drawing Sheets

Related U.S. Application Data continuation of application No. 15/312,034, filed as application No. PCT/IL2015/050532 on May 19, 2015, now Pat. No. 10,583,231, which is a continuation-in-part of application No. PCT/IL2014/050289, filed on Mar. 13, 2014.

(60) Provisional application No. 62/000,192, filed on May 19, 2014, provisional application No. 61/914,475, filed on Dec. 11, 2013, provisional application No. 61/779,803, filed on Mar. 13, 2013.

(51) Int. Cl.
*A61M 60/216* (2021.01)
*A61M 60/833* (2021.01)
*A61M 60/422* (2021.01)
*A61M 60/205* (2021.01)
*A61B 17/12* (2006.01)

(52) U.S. Cl.
CPC ........ *A61M 60/135* (2021.01); *A61M 60/205* (2021.01); *A61M 60/216* (2021.01); *A61M 60/422* (2021.01); *A61M 60/857* (2021.01); *A61B 2017/12127* (2013.01); *A61M 2205/505* (2013.01); *A61M 2205/52* (2013.01); *A61M 2205/80* (2013.01); *A61M 2230/005* (2013.01); *A61M 2230/20* (2013.01); *A61M 2230/30* (2013.01)

(58) Field of Classification Search
CPC .......... A61M 2205/52; A61M 2205/80; A61M 2230/005; A61M 2230/20; A61M 2230/30; A61B 17/12136; A61B 2017/12127

See application file for complete search history.

(56) References Cited

U.S. PATENT DOCUMENTS

| | | |
|---|---|---|
| 4,919,647 A | 4/1990 | Nash |
| 4,954,055 A | 9/1990 | Raible et al. |
| 5,613,935 A | 3/1997 | Jarvik |
| 5,713,730 A | 2/1998 | Nose et al. |
| 5,749,855 A | 5/1998 | Reitan |
| 5,772,693 A | 6/1998 | Brownlee |
| 5,876,385 A | 3/1999 | Ikari et al. |
| 5,964,694 A | 10/1999 | Siess et al. |
| 6,086,527 A | 7/2000 | Talpade |
| 6,135,729 A | 10/2000 | Aber |
| 6,136,025 A | 10/2000 | Barbut et al. |
| 6,176,848 B1 | 1/2001 | Rau et al. |
| 6,183,220 B1 | 2/2001 | Ohara et al. |
| 6,247,892 B1 | 6/2001 | Kazatchkov et al. |
| 6,482,228 B1 | 11/2002 | Norred |
| 6,533,716 B1 | 3/2003 | Schmutz-Rode et al. |
| 6,592,567 B1 | 7/2003 | Levin et al. |
| 6,616,624 B1 | 9/2003 | Kieval |
| 6,884,210 B2 | 4/2005 | Nose et al. |
| 7,004,925 B2 | 2/2006 | Navia et al. |
| 7,011,620 B1 | 3/2006 | Siess |
| 7,070,555 B2 | 7/2006 | Siess |
| 7,144,364 B2 | 12/2006 | Barbut et al. |
| 7,159,593 B2 | 1/2007 | Mccarthy et al. |
| 7,201,772 B2 | 4/2007 | Schwammenthal et al. |
| 7,335,192 B2 | 2/2008 | Keren et al. |
| 7,341,570 B2 | 3/2008 | Keren et al. |
| 7,485,104 B2 | 2/2009 | Kieval |
| 7,717,952 B2 | 5/2010 | Case et al. |
| 7,744,642 B2 | 6/2010 | Rittgers et al. |
| 7,762,941 B2 | 7/2010 | Jarvik |
| 7,766,853 B2 | 8/2010 | Lane |
| 7,766,892 B2 | 8/2010 | Keren et al. |
| 7,766,961 B2 | 8/2010 | Patel et al. |
| 7,780,628 B1 | 8/2010 | Keren et al. |
| 7,811,221 B2 | 10/2010 | Gross |
| 7,841,976 B2 | 11/2010 | McBride et al. |
| 7,914,503 B2 | 3/2011 | Goodson et al. |
| 7,927,068 B2 | 4/2011 | McBride et al. |
| 8,007,254 B2 * | 8/2011 | LaRose ................. A61M 60/81 600/16 |
| 8,012,121 B2 | 9/2011 | Goodson et al. |
| 8,079,948 B2 | 12/2011 | Shifflette |
| 8,221,492 B2 | 7/2012 | Case et al. |
| 8,235,933 B2 | 8/2012 | Keren et al. |
| 8,277,470 B2 | 10/2012 | Demarais et al. |
| 8,376,707 B2 | 2/2013 | Mcbride et al. |
| 8,449,443 B2 | 5/2013 | Rodefeld et al. |
| 8,512,262 B2 | 8/2013 | Gertner |
| 8,538,535 B2 | 9/2013 | Ariav et al. |
| 8,579,858 B2 | 11/2013 | Reitan et al. |
| 8,617,239 B2 | 12/2013 | Reitan |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 * | 5/2014 | Zeng .................... A61M 60/411 600/19 |
| 8,727,959 B2 | 5/2014 | Reitan et al. |
| 8,734,331 B2 | 5/2014 | Evans et al. |
| 8,734,508 B2 | 5/2014 | Hastings et al. |
| 8,777,832 B1 | 7/2014 | Wang et al. |
| 8,849,398 B2 | 9/2014 | Evans |
| 8,992,163 B2 | 3/2015 | McBride et al. |
| 9,028,216 B2 | 5/2015 | Schumacher et al. |
| 9,067,006 B2 | 6/2015 | Toellner |
| 9,089,634 B2 | 7/2015 | Schumacher et al. |
| 9,138,518 B2 | 9/2015 | Campbell et al. |
| 9,162,017 B2 | 10/2015 | Evans et al. |
| 9,217,442 B2 | 12/2015 | Wiessler et al. |
| 9,314,558 B2 | 4/2016 | Er |
| 9,327,067 B2 | 5/2016 | Zeng et al. |
| 9,339,596 B2 | 5/2016 | Roehn |
| 9,358,329 B2 | 6/2016 | Fitzgerald et al. |
| 9,393,384 B1 | 7/2016 | Kapur et al. |
| 9,402,942 B2 | 8/2016 | Hastie et al. |
| 9,416,783 B2 | 8/2016 | Schumacher et al. |
| 9,572,915 B2 | 2/2017 | Heuring et al. |
| 9,597,205 B2 | 3/2017 | Tuval |
| 9,675,740 B2 | 6/2017 | Zeng et al. |
| 9,750,860 B2 | 9/2017 | Schumacher |
| 9,750,861 B2 | 9/2017 | Hastie et al. |
| 9,764,113 B2 | 9/2017 | Tuval et al. |
| 9,771,801 B2 | 9/2017 | Schumacher et al. |
| 9,895,475 B2 | 2/2018 | Toellner et al. |
| 9,903,384 B2 | 2/2018 | Roehn |
| 9,907,891 B2 | 3/2018 | Wiessler et al. |
| 9,913,937 B2 | 3/2018 | Schwammenthal et al. |
| 9,964,115 B2 | 5/2018 | Scheckel |
| 10,039,874 B2 | 8/2018 | Schwammenthal et al. |
| 10,052,419 B2 | 8/2018 | Er |
| 10,107,299 B2 | 10/2018 | Scheckel |
| 10,172,985 B2 | 1/2019 | Simon et al. |
| 10,179,197 B2 | 1/2019 | Kaiser et al. |
| 10,196,899 B2 | 2/2019 | Toellner et al. |
| 10,207,037 B2 | 2/2019 | Corbett et al. |
| 10,208,763 B2 | 2/2019 | Schumacher et al. |
| 10,215,187 B2 | 2/2019 | McBride et al. |
| 10,231,838 B2 | 3/2019 | Chin et al. |
| 10,245,363 B1 | 4/2019 | Rowe |
| 10,299,918 B2 | 5/2019 | Tuval |
| 10,342,904 B2 | 7/2019 | Schumacher |
| 10,342,906 B2 | 7/2019 | D'Ambrosio et al. |
| 10,413,646 B2 | 9/2019 | Wiessler et al. |
| 10,478,538 B2 | 11/2019 | Scheckel et al. |
| 10,478,539 B2 | 11/2019 | Pfeffer et al. |
| 10,495,101 B2 | 12/2019 | Scheckel |
| 10,557,475 B2 | 2/2020 | Roehn |
| 10,583,231 B2 | 3/2020 | Schwammenthal et al. |
| 10,584,589 B2 | 3/2020 | Schumacher et al. |
| 10,589,012 B2 | 3/2020 | Toellner et al. |
| 10,617,808 B2 | 4/2020 | Hastie et al. |
| 10,662,967 B2 | 5/2020 | Scheckel |
| 10,669,855 B2 | 6/2020 | Toellner et al. |

(56) References Cited

U.S. PATENT DOCUMENTS

| | | |
|---|---|---|
| 10,765,789 B2 | 9/2020 | Zeng et al. |
| 10,792,406 B2 | 10/2020 | Roehn et al. |
| 10,799,624 B2 | 10/2020 | Pfeffer et al. |
| 10,799,626 B2 | 10/2020 | Siess et al. |
| 10,801,511 B2 | 10/2020 | Siess et al. |
| 10,806,838 B2 | 10/2020 | Er |
| 10,835,653 B2 | 11/2020 | Liebing |
| 10,857,272 B2 | 12/2020 | Liebing |
| 10,864,309 B2 | 12/2020 | McBride et al. |
| 10,865,801 B2 | 12/2020 | McBride et al. |
| 10,874,783 B2 | 12/2020 | Pfeffer et al. |
| 10,881,845 B2 | 1/2021 | Siess et al. |
| 10,894,115 B2 | 1/2021 | Pfeffer et al. |
| 10,898,629 B2 | 1/2021 | Siess et al. |
| 10,907,646 B2 | 2/2021 | Bredenbreuker et al. |
| 10,920,596 B2 | 2/2021 | Toellner et al. |
| 10,926,013 B2 | 2/2021 | Schumacher et al. |
| 10,935,038 B2 | 3/2021 | Siess |
| 10,980,927 B2 | 4/2021 | Pfeffer et al. |
| 11,007,350 B2 | 5/2021 | Tao et al. |
| 11,020,584 B2 | 6/2021 | Siess et al. |
| 11,027,114 B2 | 6/2021 | D'Ambrosio et al. |
| 11,033,729 B2 | 6/2021 | Scheckel et al. |
| 11,040,187 B2 | 6/2021 | Wiessler et al. |
| RE48,649 E | 7/2021 | Siess |
| 11,116,960 B2 | 9/2021 | Simon et al. |
| 11,123,539 B2 | 9/2021 | Pfeffer et al. |
| 11,129,978 B2 | 9/2021 | Pfeffer et al. |
| 11,167,124 B2 | 11/2021 | Pfeffer et al. |
| 11,168,705 B2 | 11/2021 | Liebing |
| 11,197,690 B2 | 12/2021 | Fantuzzi et al. |
| 11,219,755 B2 | 1/2022 | Siess et al. |
| 11,229,786 B2 | 1/2022 | Zeng et al. |
| 11,253,692 B2 | 2/2022 | Schumacher |
| 11,253,693 B2 | 2/2022 | Pfeffer et al. |
| 11,260,215 B2 | 3/2022 | Scheckel et al. |
| 11,266,824 B2 | 3/2022 | Er |
| 11,268,521 B2 | 3/2022 | Toellner |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,298,525 B2 | 4/2022 | Jahangir |
| 11,305,105 B2 | 4/2022 | Corbett et al. |
| 11,313,228 B2 | 4/2022 | Schumacher et al. |
| 11,338,124 B2 | 5/2022 | Pfeffer et al. |
| 11,351,358 B2 | 6/2022 | Nix et al. |
| 11,364,373 B2 | 6/2022 | Corbett et al. |
| 11,421,701 B2 | 8/2022 | Schumacher et al. |
| 11,434,922 B2 | 9/2022 | Roehn |
| 2002/0107536 A1 | 8/2002 | Hussein |
| 2003/0055486 A1 | 3/2003 | Adams et al. |
| 2003/0149473 A1 | 8/2003 | Chouinard et al. |
| 2003/0208097 A1 | 11/2003 | Aboul-Hosn et al. |
| 2004/0064090 A1 | 4/2004 | Keren et al. |
| 2004/0064091 A1 | 4/2004 | Keren et al. |
| 2004/0111006 A1 | 6/2004 | Alferness et al. |
| 2004/0116769 A1 | 6/2004 | Jassawalla et al. |
| 2004/0167415 A1 | 8/2004 | Gelfand et al. |
| 2004/0210236 A1 | 10/2004 | Allers et al. |
| 2004/0219028 A1 | 11/2004 | Demarais et al. |
| 2004/0260389 A1 | 12/2004 | Case et al. |
| 2005/0033406 A1 | 2/2005 | Barnhart et al. |
| 2005/0049692 A1 | 3/2005 | Numamoto et al. |
| 2005/0055082 A1 | 3/2005 | Ben et al. |
| 2005/0079274 A1 | 4/2005 | Palasis et al. |
| 2005/0119682 A1 | 6/2005 | Nguyen et al. |
| 2005/0137680 A1 | 6/2005 | Ortiz et al. |
| 2006/0062672 A1 | 3/2006 | McBride et al. |
| 2006/0064059 A1 | 3/2006 | Gelfand et al. |
| 2006/0106449 A1 | 5/2006 | Ben |
| 2006/0135961 A1 | 6/2006 | Rosenman et al. |
| 2006/0245959 A1* | 11/2006 | LaRose ............. A61M 60/824 417/423.5 |
| 2007/0100435 A1 | 5/2007 | Case et al. |
| 2007/0162103 A1 | 7/2007 | Case et al. |
| 2007/0208291 A1 | 9/2007 | Patel |
| 2007/0260327 A1 | 11/2007 | Case et al. |
| 2007/0293808 A1 | 12/2007 | Williams et al. |
| 2008/0103591 A1 | 5/2008 | Siess |
| 2008/0132748 A1 | 6/2008 | Shifflette |
| 2008/0154236 A1 | 6/2008 | Elkins et al. |
| 2008/0183280 A1 | 7/2008 | Agnew et al. |
| 2009/0024195 A1 | 1/2009 | Rezai et al. |
| 2009/0062597 A1 | 3/2009 | Shifflette |
| 2009/0093796 A1 | 4/2009 | Pfeffer et al. |
| 2009/0131785 A1 | 5/2009 | Lee et al. |
| 2009/0264991 A1 | 10/2009 | Paul et al. |
| 2009/0287299 A1 | 11/2009 | Tabor et al. |
| 2009/0318857 A1 | 12/2009 | Goodson et al. |
| 2010/0030259 A1 | 2/2010 | Pavcnik et al. |
| 2010/0130810 A1 | 5/2010 | Mohl |
| 2011/0004046 A1 | 1/2011 | Campbell et al. |
| 2011/0106244 A1 | 5/2011 | Ferrari et al. |
| 2011/0152999 A1 | 6/2011 | Hastings et al. |
| 2011/0190874 A1 | 8/2011 | Celermajer et al. |
| 2011/0213408 A1 | 9/2011 | Gross et al. |
| 2011/0230949 A1 | 9/2011 | Haverkost et al. |
| 2011/0257462 A1 | 10/2011 | Rodefeld et al. |
| 2011/0264075 A1 | 10/2011 | Leung et al. |
| 2011/0282128 A1 | 11/2011 | Reitan et al. |
| 2011/0282274 A1 | 11/2011 | Fulton |
| 2011/0301662 A1 | 12/2011 | Bar-yoseph et al. |
| 2011/0319906 A1 | 12/2011 | Rudakov et al. |
| 2012/0022579 A1 | 1/2012 | Fulton |
| 2012/0059460 A1 | 3/2012 | Reitan |
| 2012/0089047 A1 | 4/2012 | Ryba et al. |
| 2012/0116382 A1 | 5/2012 | Ku et al. |
| 2012/0130469 A1 | 5/2012 | Cragg et al. |
| 2012/0172654 A1 | 7/2012 | Bates |
| 2012/0224970 A1 | 9/2012 | Schumacher et al. |
| 2012/0232457 A1 | 9/2012 | Kandarpa |
| 2012/0237357 A1 | 9/2012 | Schumacher et al. |
| 2012/0301318 A1 | 11/2012 | Er |
| 2012/0328460 A1* | 12/2012 | Horvath ............. A61M 60/546 417/420 |
| 2013/0053623 A1 | 2/2013 | Evans et al. |
| 2013/0053732 A1 | 2/2013 | Heuser |
| 2013/0079874 A1 | 3/2013 | Doss et al. |
| 2013/0177409 A1 | 7/2013 | Schumacher et al. |
| 2013/0177432 A1 | 7/2013 | Toellner et al. |
| 2013/0237744 A1 | 9/2013 | Pfeffer et al. |
| 2014/0018840 A1 | 1/2014 | Morgan et al. |
| 2014/0025041 A1 | 1/2014 | Fukuoka et al. |
| 2014/0051908 A1 | 2/2014 | Khanal et al. |
| 2014/0128659 A1 | 5/2014 | Heuring et al. |
| 2014/0275722 A1 | 9/2014 | Zimmermann et al. |
| 2014/0350658 A1 | 11/2014 | Benary et al. |
| 2015/0018597 A1 | 1/2015 | Fierens et al. |
| 2015/0119633 A1 | 4/2015 | Haselby et al. |
| 2015/0157777 A1 | 6/2015 | Tuval et al. |
| 2015/0164662 A1 | 6/2015 | Tuval |
| 2015/0176582 A1 | 6/2015 | Liebing |
| 2015/0343136 A1 | 12/2015 | Nitzan et al. |
| 2015/0343186 A1 | 12/2015 | Nitzan et al. |
| 2016/0022890 A1 | 1/2016 | Schwammenthal et al. |
| 2016/0051741 A1 | 2/2016 | Schwammenthal et al. |
| 2016/0053768 A1 | 2/2016 | Schumacher et al. |
| 2016/0136343 A1 | 5/2016 | Anagnostopoulos |
| 2016/0184500 A1* | 6/2016 | Zeng ................ A61M 60/237 600/16 |
| 2016/0279310 A1 | 9/2016 | Scheckel et al. |
| 2017/0049946 A1 | 2/2017 | Kapur et al. |
| 2017/0071769 A1 | 3/2017 | Mangiardi |
| 2017/0100527 A1 | 4/2017 | Schwammenthal et al. |
| 2017/0197021 A1 | 7/2017 | Nitzan et al. |
| 2018/0126130 A1 | 5/2018 | Nitzan et al. |
| 2018/0149165 A1 | 5/2018 | Siess et al. |
| 2018/0169313 A1 | 6/2018 | Schwammenthal et al. |
| 2018/0303993 A1 | 10/2018 | Schwammenthal et al. |
| 2019/0175340 A1 | 6/2019 | Tuval |
| 2019/0175806 A1 | 6/2019 | Tuval et al. |
| 2019/0209758 A1 | 7/2019 | Tuval et al. |
| 2019/0239998 A1 | 8/2019 | Tuval et al. |
| 2019/0269840 A1 | 9/2019 | Tuval et al. |

(56) References Cited

U.S. PATENT DOCUMENTS

| | | |
|---|---|---|
| 2020/0254162 A1 | 8/2020 | Schwammenthal et al. |
| 2020/0288988 A1 | 9/2020 | Goldvasser |
| 2021/0236797 A1 | 8/2021 | D'Ambrosio et al. |
| 2021/0268261 A1 | 9/2021 | Tuval et al. |

FOREIGN PATENT DOCUMENTS

| | | |
|---|---|---|
| CA | 2701809 A1 | 4/2009 |
| CN | 1219136 A | 6/1999 |
| DE | 1033690 B | 7/1958 |
| DE | 10336902 B3 | 8/2004 |
| EP | 1339443 A1 | 9/2003 |
| EP | 1651290 A1 | 5/2006 |
| EP | 1827531 A1 | 9/2007 |
| EP | 1871441 A2 | 1/2008 |
| EP | 2047872 A1 | 4/2009 |
| EP | 2047873 A1 | 4/2009 |
| EP | 2217300 A1 | 8/2010 |
| EP | 2218469 A1 | 8/2010 |
| EP | 2234658 A2 | 10/2010 |
| EP | 2282070 A1 | 2/2011 |
| EP | 2298374 A1 | 3/2011 |
| EP | 2299119 A1 | 3/2011 |
| EP | 2301598 A1 | 3/2011 |
| EP | 2308524 A1 | 4/2011 |
| EP | 2314331 A1 | 4/2011 |
| EP | 2345440 A1 | 7/2011 |
| EP | 2366412 A2 | 9/2011 |
| EP | 2376788 A1 | 10/2011 |
| EP | 2408489 A1 | 1/2012 |
| EP | 2424587 A1 | 3/2012 |
| EP | 2475415 A1 | 7/2012 |
| EP | 2607712 A1 | 6/2013 |
| EP | 2040639 B1 | 2/2014 |
| EP | 2662099 B1 | 9/2014 |
| EP | 2427230 B1 | 12/2014 |
| EP | 2396050 B1 | 1/2015 |
| EP | 2835141 A1 | 2/2015 |
| EP | 2840954 A1 | 3/2015 |
| EP | 2841122 A1 | 3/2015 |
| EP | 2841124 A1 | 3/2015 |
| EP | 2860849 A1 | 4/2015 |
| EP | 2868331 A2 | 5/2015 |
| EP | 2868332 A1 | 5/2015 |
| EP | 2999496 A2 | 3/2016 |
| EP | 3000492 A1 | 3/2016 |
| EP | 3000493 A1 | 3/2016 |
| EP | 3055922 A1 | 8/2016 |
| EP | 3062730 A1 | 9/2016 |
| EP | 3108909 A1 | 12/2016 |
| EP | 3127562 A1 | 2/2017 |
| EP | 3216467 A1 | 9/2017 |
| EP | 3222302 A1 | 9/2017 |
| EP | 3287154 A1 | 2/2018 |
| EP | 3287155 A1 | 2/2018 |
| EP | 3326567 A1 | 5/2018 |
| EP | 3329951 A1 | 6/2018 |
| EP | 3338825 A1 | 6/2018 |
| EP | 3205360 B1 | 8/2018 |
| EP | 3359214 A1 | 8/2018 |
| EP | 3359215 A1 | 8/2018 |
| EP | 3398624 A1 | 11/2018 |
| EP | 3398625 A1 | 11/2018 |
| EP | 3407930 A1 | 12/2018 |
| EP | 3446729 A1 | 2/2019 |
| EP | 3446730 A1 | 2/2019 |
| EP | 3606575 A1 | 2/2020 |
| EP | 3737436 A1 | 11/2020 |
| EP | 3897814 A1 | 10/2021 |
| JP | 2012505038 A | 3/2012 |
| WO | 90/13321 | 11/1990 |
| WO | 1994/01148 A1 | 1/1994 |
| WO | 9744071 A1 | 11/1997 |
| WO | 99/34847 | 7/1999 |
| WO | 2001083016 A2 | 5/2000 |
| WO | WO-0107787 A1 * | 2/2001 ........... F04D 13/064 |
| WO | 2002070039 A2 | 3/2001 |
| WO | 0183016 A2 | 11/2001 |
| WO | 200238085 A1 | 5/2002 |
| WO | 2002038085 | 5/2002 |
| WO | 03/006096 | 1/2003 |
| WO | 04073796 | 2/2003 |
| WO | 03/103745 A2 | 12/2003 |
| WO | 2004073796 A2 | 9/2004 |
| WO | 2005020848 A2 | 3/2005 |
| WO | 2007112033 A2 | 10/2007 |
| WO | 2007127477 A2 | 11/2007 |
| WO | 2008005747 A2 | 1/2008 |
| WO | 2008055301 A1 | 5/2008 |
| WO | 2009010963 A2 | 1/2009 |
| WO | 2009091965 A1 | 7/2009 |
| WO | 2009129481 A1 | 10/2009 |
| WO | 2010133567 A1 | 11/2010 |
| WO | 2010150208 A2 | 12/2010 |
| WO | 2011035926 A1 | 3/2011 |
| WO | 2011047884 A1 | 4/2011 |
| WO | 2011076441 A1 | 6/2011 |
| WO | 2012007141 A1 | 1/2012 |
| WO | 2013032849 A1 | 3/2013 |
| WO | 2013148697 A1 | 10/2013 |
| WO | 2013183060 A2 | 12/2013 |
| WO | 2014141284 A2 | 9/2014 |
| WO | 2015063277 A2 | 5/2015 |
| WO | 2015177793 A2 | 11/2015 |
| WO | 2016185473 A1 | 11/2016 |
| WO | 2017053361 A1 | 3/2017 |
| WO | 2017081561 A1 | 5/2017 |
| WO | 2018033920 A1 | 2/2018 |
| WO | 2018061001 A2 | 4/2018 |
| WO | 2018061002 A1 | 4/2018 |
| WO | 2018078615 A1 | 5/2018 |
| WO | 2018096531 A1 | 5/2018 |
| WO | 2018158636 A1 | 9/2018 |
| WO | 2018172848 A2 | 9/2018 |
| WO | 2018220589 A1 | 12/2018 |
| WO | 2019125899 A1 | 6/2019 |
| WO | 2019138350 A2 | 7/2019 |
| WO | 2019158996 A1 | 8/2019 |
| WO | 2021159147 A1 | 8/2021 |

OTHER PUBLICATIONS

Communication Pursuant to Article 94(3) for European Patent Application No. 20179137.3 dated Nov. 9, 2021.

Examination Report for Canadian Application No. 2,948,121 dated Dec. 15, 2021.

Examination Report for Indian Application No. 201917018650 dated Dec. 9, 2021.

Final Office Action for U.S. Appl. No. 15/888,771 dated Dec. 9, 2021.

Final Office Action for U.S. Appl. No. 16/859,100 dated Jul. 13, 2022.

Issue Notification for U.S. Appl. No. 15/574,948 dated Mar. 16, 2022.

Issue Notification for U.S. Appl. No. 16/682,016 dated Mar. 23, 2022.

Issue Notification for U.S. Appl. No. 16/682,269 dated Mar. 23, 2022.

Non-Final Office Action for U.S. Appl. No. 15/888,771 dated May 25, 2022.

Non-Final Office Action for U.S. Appl. No. 16/677,893 dated Jan. 11, 2022.

Non-Final Office Action for U.S. Appl. No. 16/677,893 dated Jul. 1, 2022.

Non-Final Office Action for U.S. Appl. No. 16/682,269 dated Sep. 20, 2021.

Non-Final Office Action for U.S. Appl. No. 16/859,100 dated Apr. 29, 2022.

Notice of Allowance for U.S. Appl. No. 15/574,948 dated Jan. 27, 2022.

(56) References Cited

OTHER PUBLICATIONS

Notice of Allowance for U.S. Appl. No. 15/888,771 dated Jun. 28, 2022.
Notice of Allowance for U.S. Appl. No. 16/682,016 dated Feb. 23, 2022.
Notice of Allowance for U.S. Appl. No. 16/682,269 dated Feb. 23, 2022.
Office Action for Japanese Application No. 2019-520097 dated Oct. 26, 2021.
Extended European Search Report for European Application No. 20179137.3 dated Oct. 9, 2020.
Final Office Action for U.S. Appl. No. 16/273,898 dated Nov. 5, 2020.
International Search Report and Written Opinion from International Application No. PCT/IB2020/054759 dated Nov. 13, 2020.
Invitation to Pay Additional Fees for International Application No. PCT/IB2020/054759 dated Jul. 30, 2020.
Issue Notification for U.S. Appl. No. 16/035,871 dated Dec. 29, 2020.
Issue Notification for U.S. Appl. No. 16/278,323 dated Nov. 24, 2020.
Non-Final Office Action for U.S. Appl. No. 16/273,898 dated Feb. 17, 2021.
Non-Final Office Action for U.S. Appl. No. 16/281,385 dated Oct. 14, 2020.
Non-Final Office Action for U.S. Appl. No. 16/335,786 dated Sep. 17, 2020.
Non-Final Office Action for U.S. Appl. No. 16/345,389 dated Oct. 26, 2020.
Notice of Allowance for U.S. Appl. No. 16/035,871 dated Aug. 28, 2020.
Notice of Allowance for U.S. Appl. No. 16/035,871 dated Dec. 4, 2020.
Notice of Allowance for U.S. Appl. No. 16/278,323 dated Oct. 29, 2020.
Notice of Allowance for U.S. Appl. No. 16/281,385 dated Mar. 8, 2021.
Notice of Allowance for U.S. Appl. No. 16/335,786 dated Feb. 22, 2021.
Notice of Allowance for U.S. Appl. No. 16/345,389 dated Feb. 16, 2021.
Office Action for Australian Application No. 2020201055 dated Sep. 15, 2020.
Office Action for Chinese Application No. 201810418034.0 dated Aug. 4, 2020.
Office Action for Chinese Application No. 201810418034.0 dated Dec. 24, 2020.
Office Action for Chinese Application No. 201811196500.1 dated Aug. 28, 2020.
Office Action for Chinese Application No. 201910109564.1 dated Feb. 1, 2021.
Office Action for Japanese Application No. 2020-009045 dated Feb. 1, 2021.
Extended European Search Report for EP Patent Application No. 19212211.7 dated Mar. 31, 2020.
Extended European Search Report for EP Patent Application No. 19215724.6 dated Apr. 1, 2020.
Extended European Search Report for EP Patent Application No. 19216488.7 dated Apr. 1, 2020.
Extended European Search Report for EP Patent Application No. 19216593.4 dated Apr. 6, 2020.
Final Office Action for U.S. Appl. No. 15/574,948 dated Aug. 26, 2020.
Final Office Action for U.S. Appl. No. 15/888,771 dated Apr. 28, 2020.
Non-Final Office Action for U.S. Appl. No. 16/273,898 dated Jun. 18, 2020.
Non-Final Office Action for U.S. Appl. No. 16/278,323 dated May 22, 2020.
Communication Pursuant to Article 94(3) EPC for European Patent Application No. 19216488.7 dated Oct. 19, 2021.
Examination Report for Canadian Application No. 2,948,121 dated Jul. 8, 2021.
Issue Notification for U.S. Appl. No. 16/273,898 dated Oct. 13, 2021.
Issue Notification for U.S. Appl. No. 16/281,385 dated Jun. 16, 2021.
Issue Notification for U.S. Appl. No. 16/335,786 dated Jun. 2, 2021.
Issue Notification for U.S. Appl. No. 16/345,389 dated May 26, 2021.
Non-Final Office Action for U.S. Appl. No. 15/888,771 dated Jun. 1, 2021.
Non-Final Office Action for U.S. Appl. No. 16/242,797 dated Nov. 16, 2021.
Non-Final Office Action for U.S. Appl. No. 16/682,016 dated Sep. 20, 2021.
Notice of Allowance for U.S. Appl. No. 15/574,948 dated Nov. 18, 2021.
Notice of Allowance for U.S. Appl. No. 16/273,898 dated Jun. 30, 2021.
Office Action for Chinese Application No. 201780072633.5 dated May 26, 2021.
Office Action for Japanese Application No. 2020-93277 dated Jun. 23, 2021.
Restriction Requirement for U.S. Appl. No. 16/677,893 dated Sep. 22, 2021.
U.S. Appl. No. 16/750,354, filed Jan. 23, 2020.
U.S. Appl. No. 17/487,145, filed Sep. 28, 2021.
U.S. Appl. No. 61/656,244, filed Jun. 6, 2012.
U.S. Appl. No. 62/401,403, filed Sep. 29, 2016.
U.S. Appl. No. 62/412,631, filed Oct. 25, 2016.
U.S. Appl. No. 62/543,540, filed Aug. 10, 2017.
U.S. Appl. No. 62/615,538, filed Jan. 10, 2018.
U.S. Appl. No. 62/665,715, filed May 2, 2018.
U.S. Appl. No. 62/681,868, filed Jun. 7, 2018.
U.S. Appl. No. 62/727,605, filed Sep. 6, 2021.
Heywood, et al., "High Prevalence of Renal Dysfunction and Its Impact on Outcome in 118,465 Patients Hospitalized With Acute Decompensated Heart Failure: A Report From the ADHERE Database", Journal of Cardiac Failure, 2007, pp. 422-430.
Examination Report for European Application No. 20179137.3 dated Jan. 5, 2023.
Issue Notification for U.S. Appl. No. 15/888,771 dated Oct. 12, 2022.
Non-Final Office Action for U.S. Appl. No. 16/677,893 dated Dec. 28, 2022.
Non-Final Office Action for U.S. Appl. No. 17/320,742 dated Dec. 7, 2022.
Office Action for Japanese Application No. 2022-31553 dated Dec. 23, 2022.
"Compendium of Technical and Scientific Information for the Hemopump Temporary Cardiac Assist System", Johnson & Johnson Interventional Systems, 1988, pp. 1-15.
Achour, et al., "Mechanical Left Ventricular Unloading Prior to Reperfusion Reduces Infarct Size in a Canine Infarction Model", Catheterization and Cardiovascular Interventions 64, 2005, pp. 182-192.
Butler, et al., "The Hemopump—A New Cardiac Prothesis Device", Reprinted from IEEE Transactions on Biomedical Engineering, vol. 37, No. 2, Feb. 1990, pp. 192-195.
Chan, et al., "Rapid manufacturing techniques in the development of an axial blood pump impeller", Proc. Instn Mech. Engrs vol. 217 Part H: J. Engineering in Medicine, 2003, pp. 469-475.
Dekker, et al., "Efficacy of a New Intraaortic Propeller Pump vs the Intraaortic Balloon Pump", Chest, vol. 123, Issue 6, Jun. 2003, pp. 2089-2095.
Flameng, "Temporary Cardiac Assist with an Axial Pump System", Steinkopff Verlag Darmstadt, 1991, 79 pages.
Frazier, et al., "First Human Use of the Hemopump, a Catheter-Mounted Ventricular Assist Device", Annual of Thoracic Surgeons, vol. 49, 1990, pp. 299-304.

(56) References Cited

OTHER PUBLICATIONS

Frazier, et al., "Treatment of Cardiac Allograft Failure by use of an IntraAortic Axial Flow Pump", Journal of Heart Transplantation, St. Louis, vol. 9, No. 4, pp. 408-414, Jul. 1990.
Gunther, et al., "Experimentelle Radiologie", Life Sciences, Berichte Aus Der Rheinischwestfälischen Technischen Hochschule Aachen Ausgabe Feb. 2002, 9 pages.
Ledoux, et al., "Left Ventricular Unloading With Intra-aortic Counter Pulsation Prior to Reperfusion Reduces Myocardial Release of Endothelin-1 and Decreases Infarction Size in a Porcine Ischemia-Reperfusion Model", Catheterization and Cardiovascular Interventions 72, 2008, pp. 513-521.
Merhige, et al., "Effect of the Hemopump Left Ventricular Assist Device on Regional Myocardial Perfusion and Function", Reduction of Ischemia during Coronary Occlusion, Johnson & Johnson Interventional Systems Supplement 3, Circulation vol. 80, No. 5, Nov. 1989, pp. III-159-III-166.
Roundtree, et al., "The Hemopump Cardiac Assist System: Nursing Care of the Patient", Reprinted from Critical Care Nurse, Apr. 1991.
Scholz, et al., "MechanicaL left Ventricular Unloading During High Risk Coronary Angioplasty: First Use of a New Percutaneous Transvalvular Left Ventricular Assist Device", Catheterization and Cardiovascular Diagnosis 31, 1994, pp. 61-69.
Siess, "System Analysis and Development of Intravascular Rotation Pumps for Cardiac Assist", Helmholtz-Institute—Chapter 3, Jun. 1998, 17 pages.
Smalling, et al., "Improved Regional Myocardial Blood Flow, Left Ventricular Unloading, and Infarct Salvage Using an Axial-Flow, Transvalvular Left Ventricular Assist Device", A Comparison With Intra-Aortic Balloon Counterpulsation and Reperfusion Alone in a Canine Infarction Model, Presented in part at the American College of Cardiology 38th Annual Scientific Session, Mar. 1990, pp. 1152-1160.
Smalling, et al., "The Hemopump: A transvalvular, axial flow, left ventricular assist device", Coronary Artery Disease, Circulatory support devices in clinical cardiology, vol. 2 No. 6, pp. 666-671, Aug. 1991.
Smalling, et al., "Transvalvular Left Ventricular Assistance in Cardiogenic Shock Secondary to Acute Myocardial Infarction", Evidence for Recovery From Near Fatal Myocardial Stunning, JACC vol. 23, No. 3, pp. 637-644, Mar. 1, 1994.
Tamareille, et al., "Left ventricular unloading before reperfusion reduces endothelin-1 release and calcium overload in porcine myocardial infarction", Cardiopulmonary Support and Physiology, The Journal of Thoracic and Cardiovascular Surgery, vol. 136, No. 2, 2008, pp. 343-351.
Wampler, "Newspaper Articles", Captain Hemo, 1988, 6 pages.
Wampler, "Newsweek", Captain Hemo, May 16, 1988, 3 pages.
Wampler, "THI Today", Captain Hemo, Summer 1988, 2 pages.
Wampler, "Time Magazine", Captain Hemo, May 1988, 2 pages.
Wampler, et al., "Treatment of Cardiogenic Shock With the Hemopump Left Ventricular Assist Device", Annual of Thoracic Surgery, vol. 52, pp. 560-513, 1991.
Wampler, "U.S. News & World Report", Captain Hemo, pp. 1-2, May 16, 1988.
Communication for European Application No. 15753493.4 dated Jul. 17, 2019.
Corrected Notice of Allowance for U.S. Appl. No. 15/312,034 dated Feb. 12, 2020.
Corrected Notice of Allowance for U.S. Appl. No. 15/423,368 dated Apr. 17, 2019.
European Search Report for European Application No. 13800935 dated Jan. 12, 2016.
European Search Report for European Application No. 14762232.8 dated Sep. 28, 2016.
Final Office Action for U.S. Appl. No. 14/931,363 dated Jun. 1, 2017.
Final Office Action for U.S. Appl. No. 15/312,034 dated Jan. 17, 2019.
International Search Report and Written Opinion from International Application No. PCT/IL2015/050532 dated Jan. 27, 2016.
International Search Report and Written Opinion from International Application No. PCT/IL2016/050525 dated Oct. 14, 2016.
International Search Report and Written Opinion from International Application No. PCT/IL2017/051092 dated Jan. 16, 2018.
International Search Report and Written Opinion from International Application No. PCT/IL2017/051273 dated Apr. 17, 2018.
International Search Report and Written Opinion from International Application No. PCT/IL2019/050334 dated Jun. 17, 2019.
International Search Report and Written Opinion from International Application No. PCT/IL2013/050495 dated Nov. 22, 2013.
International Search Report and Written Opinion from International Application No. PCT/IL2014/050289 dated Sep. 11, 2014.
Invitation to pay additional fees for International Application No. PCT/IL2015/050532 dated Nov. 17, 2015.
Issue Notification for U.S. Appl. No. 14/931,363 dated Feb. 21, 2018.
Issue Notification for U.S. Appl. No. 15/312,034 dated Feb. 19, 2020.
Issue Notification for U.S. Appl. No. 15/423,368 dated May 8, 2019.
Issue Notification for U.S. Appl. No. 16/022,445 dated Jul. 10, 2019.
Non-Final Office Action for U.S. Appl. No. 14/405,144 dated Feb. 22, 2016.
Non-Final Office Action for U.S. Appl. No. 14/405,144 dated Jul. 14, 2016.
Non-Final Office Action for U.S. Appl. No. 14/567,439 dated Nov. 16, 2016.
Non-Final Office Action for U.S. Appl. No. 14/774,081 dated May 24, 2017.
Non-Final Office Action for U.S. Appl. No. 14/774,081 dated Oct. 12, 2017.
Non-Final Office Action for U.S. Appl. No. 14/931,363 dated Feb. 15, 2017.
Non-Final Office Action for U.S. Appl. No. 14/931,363 dated Oct. 3, 2016.
Non-Final Office Action for U.S. Appl. No. 15/423,368 dated Jun. 6, 2018.
Non-Final Office Action for U.S. Appl. No. 15/574,948 dated Jan. 13, 2020.
Non-Final Office Action for U.S. Appl. No. 15/888,771 dated Oct. 4, 2019.
Non-Final Office Action for U.S. Appl. No. 16/022,445 dated Aug. 9, 2018.
Non-Final Office Action for U.S. Appl. No. 16/035,871 dated Jan. 22, 2020.
Non-Final Office Action for U.S. Appl. No. 16/22,445 dated Aug. 9, 2018.
Notice of Allowance for U.S. Appl. No. 14/567,439 dated Jun. 2, 2017.
Notice of Allowance for U.S. Appl. No. 14/774,081 dated Apr. 11, 2018.
Notice of Allowance for U.S. Appl. No. 14/931,363 dated Dec. 12, 2017.
Notice of Allowance for U.S. Appl. No. 14/931,363 dated Oct. 12, 2017.
Notice of Allowance for U.S. Appl. No. 15/312,034 dated Jan. 15, 2020.
Notice of Allowance for U.S. Appl. No. 15/312,034 dated Jun. 27, 2019.
Notice of Allowance for U.S. Appl. No. 15/423,368 dated Apr. 4, 2019.
Notice of Allowance for U.S. Appl. No. 15/423,368 dated Nov. 13, 2018.
Notice of Allowance for U.S. Appl. No. 16/022,445 dated Mar. 18, 2019.
Office Action for Australian Application No. 2015262870 dated Apr. 29, 2019.
Office Action for Australian Application No. 2019202647 dated Jun. 26, 2019.
Office Action for Chinese Application No. 201380037335.4 dated Mar. 22, 2017.

(56) References Cited

OTHER PUBLICATIONS

Office Action for Chinese Application No. 201380037335.4 dated Oct. 17, 2016.
Office Action for Chinese Application No. 201810418034.0 and dated Nov. 1, 2019.
Office Action for Chinese Patent Application No. 201380037335.4 dated Sep. 20, 2017.
Office Action for European Application No. 13800935 dated Sep. 30, 2016.
Office Action for Japanese Application No. 2015/562562 dated Jan. 29, 2019.
Office Action for Japanese Application No. 2015-562562 dated Jun. 13, 2018.
Office Action for Japanese Application No. 2016/568548 dated Mar. 18, 2019.
Office Action for Japanese Patent Application No. 2015562562 dated Oct. 27, 2017.
Restriction Requirement for U.S. Appl. No. 14/567,439 dated Aug. 23, 2016.
Restriction Requirement for U.S. Appl. No. 14/774,081 dated Mar. 9, 2017.
Restriction Requirement for U.S. Appl. No. 14/931,363 dated Jul. 22, 2016.
Restriction Requirement for U.S. Appl. No. 15/888,771 dated Apr. 15, 2019.
Restriction Requirement for U.S. Appl. No. 16/035,871, dated Sep. 27, 2019.
U.S. Appl. No. 14/405,144, filed Dec. 2, 2014.
U.S. Appl. No. 14/567,439, filed Dec. 11, 2014.
U.S. Appl. No. 14/774,081, filed Sep. 9, 2015.
U.S. Appl. No. 15/423,368, filed Feb. 2, 2017.
U.S. Appl. No. 15/574,948, filed Nov. 17, 2017.
U.S. Appl. No. 16/022,445, filed Jun. 28, 2018.
U.S. Appl. No. 16/273,898, filed Feb. 12, 2019.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/278,323, filed Feb. 18, 2019.
U.S. Appl. No. 16/281,264, filed Feb. 21, 2019.
U.S. Appl. No. 16/281,385, filed Feb. 21, 2019.
U.S. Appl. No. 16/345,389, filed Apr. 26, 2019.
U.S. Appl. No. 16/677,893, filed Nov. 8, 2019.
U.S. Appl. No. 16/682,016, filed Nov. 13, 2019.
U.S. Appl. No. 16/859,100, filed Apr. 27, 2020.
U.S. Appl. No. 61/656,244, filed Jun. 6, 2013.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/425,814, filed Nov. 23, 2016.
U.S. Appl. No. 62/401,403 mailed Sep. 29, 2016.
Agarwal, et al., "Newer-generation ventricular assist devices.", Best Practice & Research Clinical Anaesthesiology, 26.2, 2012, pp. 117-130.
Alba, et al., "The future is here: ventricular assist devices for the failing heart", Expert review of cardiovascular therapy, 7.9, 2009, pp. 1067-1077.
Burnett, et al., "Renal Interstitial Pressure and Sodium Excretion During Renal Vein Constriction", American Physiological Society, 1980, pp. F279-F282.
Coxworth, "Artificial Vein Valve Could Replace Drugs for Treating Common Circulatory Problem", Published on Gizmag website (http://www.gizmag.com/artificial-venous-valve-cvi/21785/), Mar. 9, 2012.
Damman, et al., "Decreased Cardiac Output, Venous Congestion and the Association With Renal Impairment in Patients With Cardiac Dysfunction", European Journal of Heart Failure, vol. 9, 2007, pp. 872-878.
Damman, et al., "Increased Central Venous Pressure Is Associated With Impaired Renal Function and Mortality in a Broad Spectrum of Patients With Cardiovascular Disease", Journal of American College of Cardiology, vol. 53, 2009, pp. 582-588.
Doty, et al., "The Effect of Increased Renal Venous Pressure on Renal Function", The Journal of Trauma,, vol. 47(6), Dec. 1999, pp. 1000-1003.
Felker, et al., "Anemia as a Risk Factor and Therapeutic Target in Heart Failure", Journal of the American College of Cardiology, vol. 44, 2004, pp. 959-966.
Firth, et al., "Raised Venous Pressure: A Direct Cause of Sodium Retention in Oedema?", The Lancet, May 7, 1988, pp. 1033-1036.
Forman, et al., "Incidence, Predictors at Admission, and Impact of Worsening Renal Function Among Patients Hospitalized With Heart Failure", Journal of American College of Cardiology, vol. 43, 2004, pp. 61-67.
Fraser, et al., "The use of computational fluid dynamics in the development of ventricular assist devices", Medical engineering & physics, 33.3, 2011, pp. 263-280.
Gomes, et al., "Heterologous valve implantation in the infra-renal vena cava for treatment of the iliac venous valve regurgitation disease", experimental study; Rev Bras Cir Cardiovasc, 17(4), 2002, pp. 367-369.
Haddy, et al., "Effect of Elevation of Intraluminal Pressure on Renal Vascular Resistance", Circulation Research Journal of the American Heart Association, vol. 4, 1956, pp. 659-663.
Heywood, et al., "High prevalence of renal dysfunction and its impact on outcome in 118,465 patients hospitalized with acute decompensated heart failure", a report from the ADHERE database. J Cardiac Fail, vol. 13, 2007, pp. 422-430.
Hillege, et al., "Renal Function as a Predictor of Outcome in a Broad Spectrum of Patients With Heart Failure", Circulation Journal of the American Heart Association, vol. 113, 2006, pp. 671-678.
Hillege, et al., "Renal Function, Neurohormonal Activation, and Survival in Patients With Chronic Heart Failure", Circulation Journal of the American Heart Association, vol. 102, 2000, pp. 203-210.
Hsu, et al., "Review of recent patents on foldable ventricular assist devices", Recent Patents on Biomedical Engineering, 5.3, 2012, pp. 208-222.
Ikari, "The Physics of Guiding Catheter; The Ikari Guiding Catheter in TRI", available at httu:i /www.docstoc.com/docs/148136553/The-[KARI-catheter---anovel-guide-for-TRI--, uploaded on Mar. 8, 2013.
Kafagy, et al., "Design of axial blood pumps for patients with dysfunctional fontan physiology: computational studies and performance testing", Artificial organs, 39.1, 2015, pp. 34-42.
Kang, et al., "Fluid dynamics aspects of miniaturized axial-flow blood pump", Bio-medical materials and engineering, 24.1, 2014, pp. 723-729.
Koochaki, et al., "A new design and computational fluid dynamics study of an implantable axial blood pump", Australasian Physical & Engineering Sciences in Medicine, 36.4, 2013, pp. 417-422.
Lauten, et al., "Heterotopic Transcatheter Tricuspid Valve Implantation: First-In-Man Application of a Novel Approach to Tricuspid Regurgitation", European Heart Journal, (1-7 as printed), Feb. 15, 2011, pp. 1207-1213.
Mcalister, et al., "Renal Insufficiency and Heart Failure: Prognostic and Therapeutic Implications From a Prospective Cohort Study", Circulation Journal of the American Heart Association, 109, 2004, pp. 1004-1009.
Mullens, et al., "Elevated Intra-Abdominal Pressure in Acute Decompensated Heart Failure. A Potential Contributor to Worsening Renal Function", Journal of the American College of Cardiology, vol. 51, 2008, pp. 300-306.
Mullens, et al., "Importance of Venous Congestion for Worsening of Renal Function in Advanced Decompensated Heart Failure", Journal of American College of Cardiology, vol. 53, 2009, pp. 589-596.
Mullens, et al., "Prompt Reduction in Intra-Abdominal Pressure Following Large-Volume Mechanical Fluid Removal Improves Renal Insufficiency in Refractory Decompensated Heart Failure", Journal of Cardiac Failure, vol. 14, 2008, pp. 508-514.
Notarius, et al., "Central Venous Pressure During Exercise: Role of Muscle Pump", Canadian Journal of Physiology and Pharmacology, vol. 74(6), 1996, pp. 647-651.

(56) References Cited

OTHER PUBLICATIONS

Park, et al., "Nutcracker Syndrome: Intravascular Stenting Approach", Nephrol Dial Transplant, vol. 15, 2000, pp. 99-101.

Reul, et al., "Blood pumps for circulatory support", Perfusion-Sevenoaks, 15.4, 2000, pp. 295-312.

Schmitz-Rode, et al., "An Expandable Percutaneous Catheter Pump for Left Ventricular Support", Journal of the American College of Cardiology, vol. 45, 2005, pp. 1856-1861.

Semple, et al., "Effect of Increased Renal Venous Pressure on Circulatory "Autoregulation" of Isolated Dog Kidneys", Circulation Research Journal of the American Heart Association, vol. 7, 1959, pp. 643-648.

Song, et al., "Axial flow blood pumps", ASAIO journal, 49, 2003, pp. 355-364.

Tang, et al., "Anemia in Chronic Heart Failure: Prevalence, Etiology, Clinical Correlates, and Treatment Options", Circulation Journal of the American Heart Association, vol. 113, 2006, pp. 2454-2461.

Throckmorton, et al., "Design of a protective cage for an intravascular axial flow blood pump to mechanically assist the failing Fontan", Artificial organs, 33.8, 2009, pp. 611-621.

Thunberg, et al., "Ventricular assist devices today and tomorrow", Journal of cardiothoracic and vascular anesthesia, 24.4, 2010, pp. 656-680.

Timms, "A review of clinical ventricular assist devices", Medical engineering & physics, 33.9, 2011, pp. 1041-1047.

Uthoff, et al., "Central venous pressure at emergency room presentation predicts cardiac rehospitalization in patients with decompensated heart failure", European Journal of Heart Failure, 12, 2010, pp. 469-476.

Wencker, "Acute Cardio-Renal Syndrome: Progression From Congestive Heart Failure to Congestive Kidney Failure", Current Heart Failure Reports, vol. 4, 2007, pp. 134-138.

Winton, "The Control of Glomerular Pressure by Vascular Changes Within the Mammalian Kidney, Demonstrated by the Actions of Adrenaline", Journal of Physiology, vol. 73, Nov. 1931, pp. 151-162.

Winton, "The Influence of Venous Pressure on the Isolated Mammalian Kidney", Journal of Physiology, vol. 72(1), Jun. 6, 1931, pp. 49-61.

Wood, "The Mechanism of the Increased Venous Pressure With Exercise in Congestive Heart Failure", Journal of Clinical Investigation, vol. 41(11), 1962, pp. 2020-2024.

Wu, et al., "Design and simulation of axial flow maglev blood pump", International Journal of Information Engineering and Electronic Business, 3.2, 2011, p. 42.

Yancy, et al., "Clinical Presentation, Management, and In-Hospital Outcomes of Patients Admitted With Acute Decompensated Heart Failure With Preserved Systolic Function. A Report From the Acute Decompensated Heart Failure National Registry (ADHERE) Database", Journal of the American College of Cardiology, vol. 47(1), 2006, pp. 76-84.

\* cited by examiner

BLOOD PUMP

CROSS-REFERENCES TO RELATED APPLICATIONS

The present is a continuation of U.S. patent application Ser. No. 15/888,771 to Schwammenthal, filed Feb. 5, 2018 (published as US 2018/0228951), which is a continuation of U.S. patent application Ser. No. 15/312,034 to Schwammenthal, Nov. 17, 2016 (issued as U.S. Ser. No. 10,583,231 on Mar. 10, 2020), which is a US national phase application of PCT Application No. PCT/IL/2015/050532 to Schwammenthal (published as WO 15/177793), filed May 19, 2015, which:

(a) claims priority from US Provisional Patent Application 62/000,192 to Schwammenthal, filed May 19, 2014, entitled "Blood pump:" and (b) is a continuation-in-part of International Patent Application PCT/IL2014/050289 to Schwammenthal (published as WO 14/141284), filed Mar. 13, 2014, entitled "Renal pump," which claims priority from (a) US Provisional Patent Application 61/779,803 to Schwammenthal, filed Mar. 13, 2013, entitled "Renal pump," and (b) US Provisional Patent Application 61/914,475 to Schwammenthal, filed Dec. 11, 2013, entitled "Renal pump."

All of the above-referenced applications are incorporated herein by reference.

FIELD OF EMBODIMENTS OF THE INVENTION

Some applications of the present invention generally relate to medical apparatus.

Specifically, some applications of the present invention relate to apparatus and methods associated with placing a pump in one or more of a subject's renal veins, and/or in the subject's vena cava.

BACKGROUND

It is common for cardiac dysfunction or congestive heart failure to develop into kidney dysfunction, which in turn, causes congestive heart failure symptoms to develop or worsen. Typically, systolic and/or diastolic cardiac dysfunction causes systemic venous congestion, which gives rise to an increase in renal venous and interstitial pressure. The increase in the pressure causes fluid retention by the body to increase due both to kidney dysfunction and renal neurohormonal activation, both of which typically develop as a result of the increase in renal venous and interstitial pressure. The resulting fluid retention causes congestive heart failure to develop or worsen, by causing a blood volume overload at the heart and/or by increasing systemic resistance. Similarly, it is common for kidney dysfunction and/or renal neurohormonal activation to develop into cardiac dysfunction and/or congestive heart failure. This pathophysiological cycle, in which cardiac dysfunction and/or congestive heart failure leads to kidney dysfunction and/or renal neurohormonal activation, or in which kidney dysfunction and/or renal neurohormonal activation leads to cardiac dysfunction and/or congestive heart failure, each dysfunction leading to deterioration in the other dysfunction, is called the cardio-renal syndrome.

Increased renal venous pressure has been experimentally shown to cause azotemia, and a reduction in glomerular filtration rate, renal blood flow, urine output, and sodium excretion. It has also been shown to increase plasma renin and aldosterone, and protein excretion. Venous congestion may also contribute to anemia via three different pathways: A reduction in the kidney's erythropoietin production, hemodilution by fluid retention, and an inflammatory response leading to a reduced gastro-intestinal iron uptake.

Mechanistically, increased renal venous pressure may cause intracapsular pressure and, subsequently interstitial peritubular pressure, to rise. A rise in peritubular pressure may impact tubular function (reduce sodium excretion), as well as diminish glomerular filtration by raising the pressure in the Bowman capsule.

In heart failure patients, increased renal venous pressure may not only result from increased central venous (right atrial) pressure, but also from intraperitoneal fluid accumulations (ascites) exerting direct pressure on the renal veins. Reduction of intraabdominal pressure in heart failure patients by removal of fluid (e.g., via paracentesis, and/or ultrafiltration) has been shown to reduce plasma creatinine levels.

Increased venous return resulting from activation of the "leg muscle pump" during physical activity such as walking may raise systemic venous pressure, particularly in heart failure patients, and may result in reflux into the renal veins.

SUMMARY OF EMBODIMENTS

In accordance with some applications of the present invention, a subject is identified as suffering from cardiac dysfunction, congestive heart failure, reduced renal blood flow, increased renal vascular resistance, arterial hypertension, diabetes, and/or kidney dysfunction. In response thereto, blood pressure within the subject's renal veins is reduced by placing at least one pump in the subject's vena cava, and generating a low-pressure region within the subject's vena cava adjacent to junctions of the vena cava with the subject's renal veins, by activating the pump to pump blood away from the region. The pump is activated such that blood pressure within the low-pressure region is lower than central venous pressure of the subject. Typically, a downstream pump is placed within the vena cava downstream of the junctions of the vena cava with the subject's renal veins, and the pump pumps blood through the vena cava in the downstream direction, away from the junctions. For some applications, an upstream pump is placed within the vena cava upstream of the junctions of the vena cava with the subject's renal veins, and the pump pumps blood through the vena cava in the upstream direction, away from the junctions. Alternatively or additionally, an occlusion element, such as a balloon or a covered stent is placed in the vena cava upstream of the junctions, and is configured to partially occlude the vena cava upstream of the junctions.

For some applications, the upstream and downstream pumps are disposed on a single catheter. Typically, the catheter is inserted into the vena cava via a venous pathway, e.g., via the femoral vein, via the subclavian vein, or via the jugular vein. For some applications, the upstream pump, or the occlusion element is disposed on a first catheter, which is inserted via a vein that is below the subject's inferior vena cava (e.g., the femoral vein), and the downstream pump is disposed on a second catheter, which is inserted via a vein that is above the subject's inferior vena cava (e.g., the subclavian vein, or the jugular vein).

For some applications, the downstream pump and/or the upstream pump includes an impeller and a cage. For some applications, impellers of the downstream and the upstream pumps rotate in the same direction, but the downstream pump is configured to pump blood in the downstream direction and the upstream pump is configured to pump blood in the upstream direction. For some such applications, a single motor is used to impart rotational motion to both of the impellers, and there is a shaft disposed between the impellers that imparts rotational motion from a first one of the impellers to a second one of the impellers. Typically, for such applications, the impellers of the upstream and the downstream pumps are (a) of opposing handedness with respect to one another (i.e., one of the impellers is a left-handed impeller, and the other impeller is a right-handed impeller), and (b) are disposed upon the aforementioned shaft, such that the impellers are facing opposite directions to one another.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

In general, in the specification and in the claims of the present application, the term "downstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is downstream, with respect to the direction of antegrade blood flow through the blood vessel, relative to a different location within the blood vessel. The term "upstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is upstream with respect to the direction of antegrade blood flow through the blood vessel, relative to a different location within the blood vessel.

There is therefore provided, in accordance with some applications of the present invention, apparatus including:
 a catheter;
 a first pump disposed on the catheter;
 a second pump disposed on the catheter, proximally to the first pump; and
 a control unit configured to control activation of the first and second pumps,
 the first and second pumps being configured, when activated, to pump fluid in opposite directions from one another.

For some applications, the catheter is configured to be placed within a vena cava of a subject such that the first pump is disposed downstream of junctions of the vena cava with all renal veins of the subject, and such that the second pump is disposed upstream of junctions of the vena cava with all renal veins of the subject.

For some applications, the first and second pumps are configured to lower pressure within the subject's renal veins by:
 the first pump pumping blood through the vena cava in a downstream direction, and
 the second pump pumping blood through the vena cava in an upstream direction.

For some applications, the catheter is configured to be placed within the subject's vena cava by being inserted via a vein of the subject selected from the group consisting of: a subclavian vein, a jugular vein, and a femoral vein.

For some applications:
 the first pump includes a first impeller configured to pump blood through the vena cava by rotating; and
 the second pump includes a second impeller configured to pump blood through the vena cava by rotating.

For some applications,
 the apparatus further includes a first cage, the first impeller being disposed inside the first cage, and the first cage configured to maintain a separation between the first impeller and an inner wall of the vena cava; and
 the apparatus further includes a second cage, the second impeller being disposed inside the second cage, and the second cage being configured to maintain a separation between the second impeller and the inner wall of the vena cava.

For some applications, the first and second impellers are configured, when activated, to pump blood in opposite directions from one another by the first and second impellers being rotated in the same direction as one another, as viewed from an external reference point.

For some applications, the first and second impellers are of opposing-handedness with respect to one another, and are disposed upon the catheter such that the impellers face opposite directions from one another.

For some applications, the catheter is configured to be placed within a blood vessel of a subject, and the first and second pumps are configured to generate a region within the blood vessel that is of lower blood pressure than elsewhere within the blood vessel by pumping blood away from a region of the blood vessel between the first and second pumps.

For some applications, the catheter is configured to be placed within a main vein of a subject into which blood flows from a tributary venous system such that:
 the first pump is placed in the main vein, downstream of the tributary venous system; and
 the second pump is placed in the main vein, upstream of the tributary venous system.

For some applications, the catheter is configured to be placed within a blood vessel of a subject, and the first and second pumps are configured to generate a region within the blood vessel that is of higher blood pressure than elsewhere within the blood vessel by pumping blood toward a region of the blood vessel between the first and second pumps.

For some applications, the catheter is configured to be placed within a main artery of a subject that supplies a branching arterial system that branches from the main artery such that:
 the first pump is placed in the main artery, downstream of the branching arterial system; and
 the second pump is placed in the main artery, upstream of the branching arterial system.

For some applications:
 the first pump includes a first impeller configured to pump fluid by rotating; and
 the second pump includes a second impeller configured to pump fluid by rotating.

For some applications, the first and second impellers are configured, when activated, to pump fluid in opposite directions from one another by the first and second impellers being rotated in the same direction as one another, as viewed from an external reference point.

For some applications, the first and second impellers are of opposing-handedness with respect to one another, and are disposed upon the catheter such that the impellers face opposite directions from one another.

For some applications, the apparatus further includes a motor configured to cause the first and second impellers to pump fluid in opposite directions from one another by rotating the first and second impellers in the same direction as one another.

There is further provided, in accordance with some applications of the present invention, apparatus including:
a catheter;
a first impeller disposed on the catheter; and
a second impeller disposed on the catheter, proximally to the first impeller,
longitudinal centers of the first and second impellers being separated from one another by a distance of at least 3 cm, the distance being measured along a longitudinal axis of the catheter.

For some applications, the first and second impellers are of opposing-handedness with respect to one another, and are disposed upon the catheter such that the impellers face opposite directions from one another.

For some applications, the catheter is configured to be placed within a vena cava of a subject such that the first impeller is disposed downstream of junctions of the vena cava with all renal veins of the subject, and such that the second impeller is disposed upstream of junctions of the vena cava with all renal veins of the subject.

For some applications, the catheter is configured to be placed within the subject's vena cava by being inserted via a vein of the subject selected from the group consisting of: a subclavian vein, a jugular vein, and a femoral vein.

For some applications:
the apparatus further includes a first cage, the first impeller being disposed inside the first cage, and the first cage being configured to maintain a separation between the first impeller and an inner wall of the vena cava; and
the apparatus further includes a second cage, the second impeller being disposed inside the second cage, and the second cage being configured to maintain a separation between the second impeller and the inner wall of the vena cava.

For some applications,
the apparatus further includes a control unit configured to control rotation of the first and second impellers, and
the first and second impellers are configured, by rotating, to lower pressure within the subject's renal veins by:
the first impeller pumping blood through the vena cava in a downstream direction, and
the second impeller pumping blood through the vena cava in an upstream direction.

For some applications, the first and second impellers are configured to pump fluid in opposite directions from one another by the first and second impellers rotating in the same direction as one another, as viewed from an external reference point.

For some applications, the first and second impellers are of opposing-handedness with respect to one another, and are disposed upon the catheter such that the impellers face opposite directions from one another.

For some applications,
the apparatus further includes a control unit configured to control rotation of the first and second impellers, and
the first and second impellers are configured to pump fluid in opposite directions from one another, by the first and second impellers rotating in the same direction as one another, as viewed from an external reference point.

For some applications, the first and second impellers are of opposing-handedness with respect to one another, and are disposed upon the catheter such that the impellers face opposite directions from one another.

For some applications, the apparatus further includes a motor configured to cause the first and second impellers to pump fluid in opposite directions from one another by rotating the first and second impellers in the same direction as one another.

For some applications, the catheter is configured to be placed within a blood vessel of a subject, and the first and second impellers are configured to generate a region within the blood vessel that is of lower blood pressure than elsewhere within the blood vessel by pumping blood away from a region of the blood vessel between the first and second impellers.

For some applications, the catheter is configured to be placed within a main vein of a subject into which blood flows from a tributary venous system such that:
the first impeller is placed in the main vein, downstream of the tributary venous system; and
the second impeller is placed in the main vein, upstream of the tributary venous system.

For some applications, the catheter is configured to be placed within a blood vessel of a subject, and the first and second impellers are configured to generate a region within the blood vessel that is of higher blood pressure than elsewhere within the blood vessel by pumping blood toward a region of the blood vessel between the first and second impellers.

For some applications, the catheter is configured to be placed within a main artery of a subject that supplies a branching arterial system that branches from the main artery such that:
the first impeller is placed in the main artery, downstream of the branching arterial system; and
the second impeller is placed in the main artery, upstream of the branching arterial system.

There is additionally provided, in accordance with some applications of the present invention, apparatus including:
a catheter configured to be placed inside a blood vessel of a subject;
a blood pump disposed on the catheter; and
an occlusion element disposed on the catheter, and configured to partially occlude the subject's blood vessel,
longitudinal centers of the blood pump and the occlusion element being separated from one another by a distance of at least 3 cm, the distance being measured along a longitudinal axis of the catheter.

For some applications, the blood pump includes an impeller configured to pump blood through the subject's blood vessel by rotating.

For some applications, the apparatus further includes a cage, the impeller being disposed inside the cage, and the cage being configured to maintain a separation between the impeller and an inner wall of the blood vessel.

For some applications, the catheter is configured to be placed within a vena cava of a subject such that the blood pump is disposed downstream of junctions of the vena cava with all renal veins of the subject, and such that the occlusion element is disposed upstream of junctions of the vena cava with all renal veins of the subject.

For some applications, the blood pump is configured to lower pressure within the subject's renal veins by pumping blood through the vena cava in a downstream direction.

For some applications, the catheter is configured to be placed within the subject's vena cava by being inserted via a vein of the subject selected from the group consisting of: a subclavian vein, a jugular vein, and a femoral vein.

For some applications, the blood pump includes an impeller configured to pump blood through the vena cava by rotating.

For some applications, the apparatus further includes a cage, the impeller being disposed inside the cage, and the cage being configured to maintain a separation between the impeller and an inner wall of the vena cava.

For some applications, the blood pump and the occlusion element are configured to generate a region within the blood vessel that is of lower blood pressure than elsewhere within the blood vessel by the blood pump pumping away from a region of the blood vessel between the blood pump and the occlusion element.

For some applications, the catheter is configured to be placed within a main vein of a subject into which blood flows from a tributary venous system such that:

the blood pump is placed in the main vein, downstream of the tributary venous system; and the occlusion element is placed in the main vein, upstream of the tributary venous system.

For some applications, the blood pump and occlusion element are configured to generate a region within the blood vessel that is of higher blood pressure than elsewhere within the blood vessel by the blood pump pumping blood toward a region of the blood vessel between the blood pump and the occlusion element.

For some applications, the catheter is configured to be placed within a main artery of a subject that supplies a branching arterial system that branches from the main artery such that:

the occlusion element is placed in the main artery, downstream of the branching arterial system; and the blood pump is placed in the main artery, upstream of the branching arterial system.

There is further provided, in accordance with some applications of the present invention, a method for use with a tributary venous system of a subject that flows into a main vein of the subject, the method including:

reducing blood pressure within the tributary venous system by:

placing a first pump in the main vein, downstream of the tributary venous system, and activating the first pump to pump blood through the main vein in a downstream direction; and placing a second pump in the main vein, upstream of the tributary venous system, and activating the second pump to pump blood through the main vein in an upstream direction.

For some applications, the first and second pumps are disposed upon a single catheter, and placing the first and second pumps in the main vein includes inserting a distal end of the catheter into the main vein.

For some applications:

the main vein includes a vena cava of the subject, the tributary venous system includes a renal venous system of the subject, placing the first pump in the main vein downstream of the tributary venous system, includes placing the first pump in the vena cava, downstream of junctions of the vena cava with all renal veins of the subject, placing the second pump in the main vein, upstream of the tributary venous system, includes placing the second pump in the vena cava, upstream of the junctions of the vena cava with all of the subject's renal veins, the method further includes identifying the subject as suffering from a condition selected from the group consisting of: cardiac dysfunction, congestive heart failure, reduced renal blood flow, increased renal vascular resistance, arterial hypertension, and kidney dysfunction, and reducing pressure within the tributary venous system includes reducing pressure within renal veins of the subject, in response to the identifying.

For some applications, the first and second pumps are disposed upon a single catheter, and placing the first and second pumps in the vena cava includes inserting a distal end of the catheter into the subject's vena cava.

For some applications, inserting the distal end of the catheter into the subject's vena cava includes inserting the distal end of the catheter into the subject's vena cava via a vein of the subject selected from the group consisting of: a subclavian vein, a jugular vein, and a femoral vein.

For some applications:

placing the first pump in the main vein includes placing a first impeller in the main vein, downstream of the tributary venous system; and placing the second pump in the main vein includes placing a second impeller in the main vein, upstream of the tributary venous system.

For some applications:

placing the first impeller inside the main vein includes inserting the first impeller into the main vein while the first impeller is disposed inside a cage that is configured to maintain a separation between the first impeller and an inner wall of the main vein; and placing the second impeller inside the main vein includes inserting the second impeller into the main vein while the second impeller is disposed inside a cage that is configured to maintain a separation between the second impeller and the inner wall of the main vein.

For some applications, activating the first pump to pump blood through the main vein in the downstream direction includes rotating the first impeller in a given direction, and activating the second pump to pump blood through the main vein in the upstream direction includes rotating the second impeller in the same given direction, as viewed from an external reference point.

For some applications, the first and second impellers are of opposing-handedness to one another, and are disposed upon a single catheter such that the first and second impellers face in opposite directions from another, and placing the first and second pumps in the vena cava includes inserting a distal end of the catheter into the subject's vena cava.

For some applications, rotating the first and second impellers in the given direction includes using a single motor to rotate the first and second impellers.

There is additionally provided, in accordance with some applications of the present invention, a method for use with a tributary venous system of a subject that flows into a main vein of the subject, the method including:

reducing blood pressure within the tributary venous system by:

placing a pump in the main vein, downstream of the tributary venous system, and activating the pump to pump blood through the main vein in a downstream direction; and placing an occlusion element in the main vein at a location within the main vein that is upstream of the tributary venous system, such that the occlusion element partially occludes the main vein at the location.

For some applications, placing the occlusion element in the main vein includes placing a balloon in the main vein.

For some applications, placing the occlusion element in the main vein includes placing a frame that is covered with a blood-impermeable material in the main vein.

For some applications, the pump and the occlusion element are disposed upon a single catheter, and placing the pump and the occlusion element in the main vein includes inserting a distal end of the catheter into the main vein.

For some applications:
the main vein includes a vena cava of the subject,
the tributary venous system includes a renal venous system of the subject,
placing the pump in the main vein, downstream of the tributary venous system includes placing the pump in the vena cava, downstream of junctions of the vena cava with all renal veins of the subject,
placing the occlusion element in the main vein at the location within the main vein that is upstream of the tributary venous system includes placing the occlusion element in the vena cava upstream of the junctions of the vena cava with all of the subject's renal veins,
the method further includes identifying the subject as suffering from a condition selected from the group consisting of: cardiac dysfunction, congestive heart failure, reduced renal blood flow, increased renal vascular resistance, arterial hypertension, and kidney dysfunction, and
reducing pressure within the tributary venous system includes reducing pressure within renal veins of the subject, in response to the identifying.

For some applications, the pump and the occlusion element are disposed upon a single catheter, and placing the pump and the occlusion element in the vena cava includes inserting a distal end of the catheter into the vena cava.

For some applications, inserting the distal end of the catheter into the vena cava includes inserting the distal end of the catheter into the vena cava via a vein of the subject selected from the group consisting of: a subclavian vein, a jugular vein, and a femoral vein.

For some applications, placing the pump in the main vein includes placing an impeller in the main vein, downstream of the tributary venous system.

For some applications, placing the impeller inside the main vein includes inserting the first impeller into the main vein while the impeller is disposed inside a cage that is configured to maintain a separation between the first impeller and an inner wall of the main vein.

There is further provided, in accordance with some applications of the present invention, a method including:
identifying a subject as suffering from a condition selected from the group consisting of: cardiac dysfunction, congestive heart failure, reduced renal blood flow, increased renal vascular resistance, arterial hypertension, and kidney dysfunction; and
in response thereto, reducing blood pressure within renal veins of the subject, by:
placing at least one pump in a vena cava of the subject; and
generating a low-pressure region within the subject's vena cava, adjacent to junctions of the vena cava with the subject's renal veins, blood pressure within the low-pressure region being lower than central venous pressure of the subject,
by activating the at least one pump to pump blood away from the region.

For some applications, generating the low-pressure region within the subject's vena cava includes:
placing a blood-impermeable sleeve in the subject's vena cava, such that a downstream end of the sleeve is coupled to a wall of the vena cava at a first location that is downstream of all of the renal veins of the subject, and such that an upstream end of the sleeve is coupled to the wall of the vena cava at a second location that is upstream of all the renal veins of the subject; and
activating the pump to pump blood from a location outside the sleeve that is in fluid communication with the subject's renal veins, to a location within the vena cava that is in fluid communication with an interior of the sleeve.

For some applications:
placing the at least one pump in the subject's vena cava includes:
placing a first pump in the vena cava, downstream of junctions of the vena cava with all renal veins of the subject; and
placing a second pump in the vena cava, upstream of the junctions of the vena cava with all of the subject's renal veins; and generating the low-pressure region within the subject's vena cava includes:
activating the first pump to pump blood through the vena cava in a downstream direction; and
activating the second pump to pump blood through the vena cava in an upstream direction.

For some applications:
placing the at least one pump in the subject's vena cava includes:
placing a pump in the vena cava, downstream of junctions of the vena cava with all renal veins of the subject; and
placing an occlusion element in the vena cava at a location within the vena cava that is upstream of the junctions of the vena cava with all of the subject's renal veins, such that the occlusion element partially occludes the vena cava at the location; and
generating the low-pressure region within the subject's vena cava includes activating the pump to pump blood through the vena cava in a downstream direction.

For some applications, placing the occlusion element in the vena cava includes placing a balloon in the vena cava.

For some applications, placing the occlusion element in the vena cava includes placing in the vena cava a frame that is covered with a blood-impermeable material.

The present invention will be more fully understood from the following detailed description of embodiments thereof, taken together with the drawings, in which:

DETAILED DESCRIPTION OF EMBODIMENTS

Figure 1A:
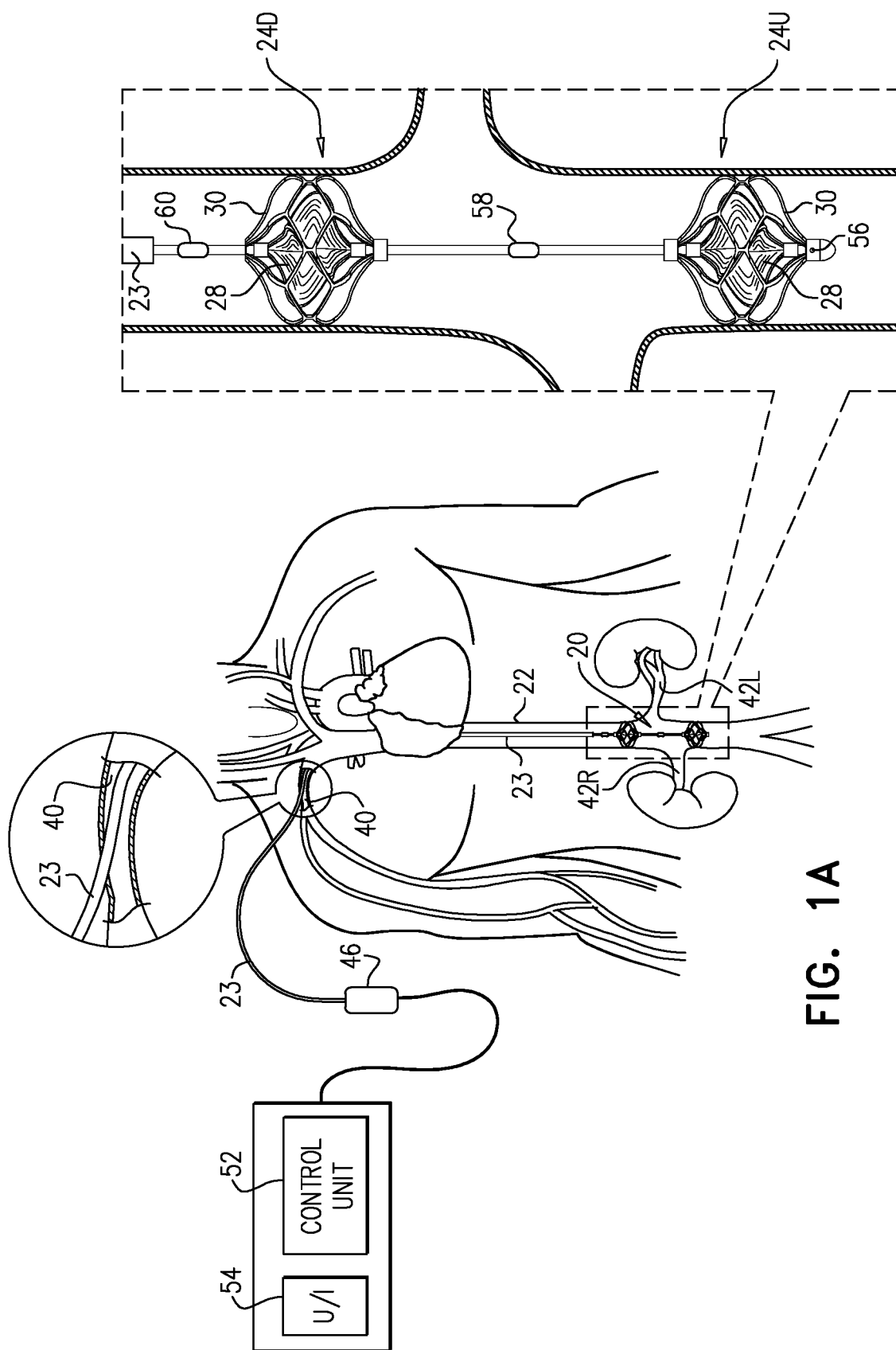
FIGS. 1A-1D are schematic illustrations of a blood-pump catheter placed within a subject's vena cava, an upstream pump being disposed upon the catheter, distally to a downstream pump, in accordance with some applications of the present invention.
Figure 1B:
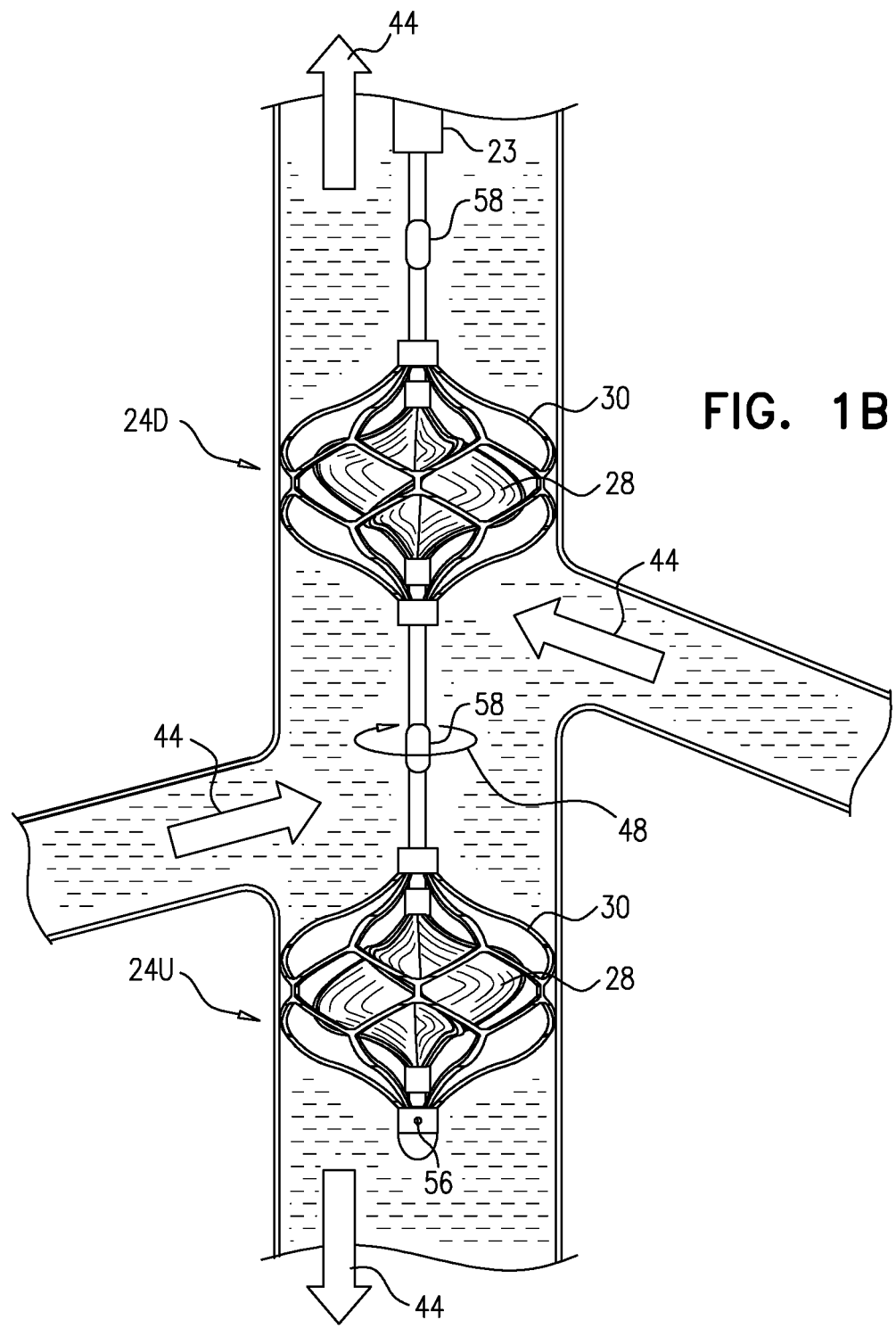

Reference is made to FIGS. 1A-D, which are schematic illustrations of a blood-pump catheter 20 placed within a subject's vena cava 22, via a guide catheter 23, an upstream pump 24U being disposed upon the catheter, distally to a downstream pump 24D, in accordance with some applications of the present invention. Typically, the distal portion of blood-pump catheter 20 is configured to be straight, when the catheter is in a non-constrained state, such that both the upstream and the downstream pumps are disposed along the axis of the catheter, within the vena cava.

Each of the upstream and downstream pumps 24U and 24D typically includes a radially-expandable impeller 28 disposed inside a radially-expandable impeller cage 30. Typically, impeller 28 and cage 30 are shape set such as to assume radially-expanded configurations thereof in the absence of any radially-constraining force acting upon the impeller and the cage. Further typically, an engagement mechanism engages the impeller and the cage with respect to one another, such that in response to the cage becoming radially constrained the impeller becomes radially constrained, e.g., in accordance with apparatus and methods described in described in WO 14/141284 to Schwammenthal, which is incorporated herein by reference.

It is noted that the term "impeller" is used herein to denote a bladed rotor, as shown in 1A-D, for example. When the bladed rotor is placed inside a blood vessel (such as vena cava 22) and rotated, the bladed rotor functions as an impeller, by modifying the flow of blood through the blood vessel, and/or by generating a pressure difference between the upstream end and the downstream end of the impeller.

It is noted that reference numeral 24 is generally used to denote a blood pump in the present application. When a pump that is placed upstream is being referred to, reference numeral 24U is used, and when a pump that is placed downstream is being referred to, reference numeral 24D is used. Similarly, reference numeral 28 is generally used to denote an impeller in the present application. When an impeller that is placed upstream is being referred to, reference numeral 28U is used, and when an impeller that is placed downstream is being referred to, reference numeral 28D is used.

Blood-pump catheter 20 is typically placed inside the subject's vena cava 22, and operated therein, in order to provide acute treatment of a subject suffering from cardiac dysfunction, congestive heart failure, low renal blood flow, high renal vascular resistance, arterial hypertension, diabetes, and/or kidney dysfunction. For example, the blood-pump catheter may be placed inside the subject's vena cava, and operated therein, for a period of more than one hour (e.g., more than one day), less than one week (e.g., less than four days), and/or between one hour and one week (e.g., between one day and four days). For some applications, the blood-pump catheter is chronically placed inside the subject's vena cava in order to provide chronic treatment of a subject suffering from cardiac dysfunction, congestive heart failure, low renal blood flow, high renal vascular resistance, arterial hypertension, diabetes, and/or kidney dysfunction. For some applications, a course of treatment is applied to a subject over several weeks, several months, or several years, during which the blood-pump catheter is intermittently placed inside the subject's vena cava, and the subject is intermittently treated in accordance with the techniques described herein. For example, the subject may be intermittently treated at intervals of several days, several weeks, or several months.

For some applications, blood-pump catheter 20 is inserted into vena cava 22, via the subject's subclavian vein 40, as shown in FIG. 1A. Typically, the blood-pump catheter is inserted under fluoroscopic imaging. Alternatively, the blood-pump catheter is inserted under ultrasound imaging, such as to reduce exposure of the subject to radiation and/or contrast agent. The catheter is placed into the vena cava such that upstream pump 24U is disposed upstream of the junctions of the vena cava and all of the subject's renal veins 42, and such that downstream pump 24D is disposed downstream of the junctions of the vena cava and all of the subject's renal veins. Typically, the upstream pump is configured to pump blood through the vena cava in the upstream direction, away from the renal veins, and the downstream pump is configured to pump blood through the vena cava in the downstream direction, away from the renal veins.

The effect of both of pumps 24U and 24D pumping blood in the above-described manner is that, between the pumps, and adjacent to the junctions of the vena cava with the renal veins, there is a low-pressure region of the vena cava, within which blood pressure is lower than the subject's central venous pressure. Functionally, this region may be viewed as a compartment within the vena cava within which blood pressure is controlled (by controlling pumps 24U and 24D), regardless of the blood pressure elsewhere within the vena cava. This typically increases blood flow from the renal veins into the vena cava, lowers pressure within the subject's renal veins, and causes renal perfusion to increase. The effect of pumps 24U and 24D on blood flow through the renal veins and the vena cava is indicated by arrows 44 in FIG. 1B.

As described hereinabove, the effect of operating blood pumps 24U and 24D is that between the pumps there is a low-pressure region of the vena cava. However, typically, the pumps are operated simultaneously such that the pressure within other portions of the vena cava is substantially unchanged relative to when blood-pump catheter 20 is not in operation. For example, the pumps are typically operated simultaneously such that the pressure within the vena cava downstream of downstream pump 24D is not substantially increased relative to when blood-pump catheter 20 is not in operation. Similarly, the pumps are typically operated simultaneously such that the pressure within the vena cava upstream of upstream pump 24U is not substantially increased relative to when blood-pump catheter 20 is not in operation. This is because the pumps are typically operated simultaneously such that outside of the region between the two pumps, the effects of the pumping by the upstream and downstream pumps cancel each other with respect to pressure. It is noted that there is likely to be some increase in the pressure within the vena cava downstream of downstream pump and upstream of upstream pump due to the increased blood flow from the renal veins into the vena cava.

Similarly, the pumps are typically operated simultaneously such that venous return to the vena cava from regions upstream of the upstream pump and downstream from the downstream pump is substantially unchanged relative to when blood-pump catheter 20 is not in operation. In this manner, the pumps the pumps are typically operated simultaneously such as to have a generally synergistic effect on pressure and flow in the region between the pumps, but to have an antagonistic effect on pressure and flow outside of the region, such that, outside of the region, the effects of the two pumps typically substantially cancel each other.

Typically, blood-pump catheter 20 pumps blood in a manner that enhances the rate of flow of blood flow through the renal veins and into the vena cava, but does not cause a substantial change in the direction of the blood flow relative to the natural direction of flow through the renal veins, or from the renal veins to the vena cava (i.e., relative to blood flow in the absence of pumping by the blood-pump catheter). That is to say that the blood-pump catheter pumps blood in the downstream direction through the renal veins and then directly into the portion of the vena cava that is adjacent to the renal veins, rather than, for example, pumping the blood from the renal veins into a different portion of the subject's veins (such as, an upstream location within the vena cava). It is noted that, due to the pumping of the downstream pump in the downstream direction, there is likely to be some blood flow from the renal veins to the portion of the vena cava that is below the renal veins. Further typically, blood-pump catheter 20 enhances blood flow through the renal veins without removing blood from the subject's venous system into a non-venous receptacle, such as an artificial lumen of a blood pump.

As described hereinabove, typically blood-pump catheter 20 is placed inside the vena cava of a subject suffering from cardiac dysfunction, congestive heart failure, low renal blood flow, high renal vascular resistance, arterial hypertension, diabetes, and/or kidney dysfunction. Typically, operating the blood-pump catheter in the vena cava of such a subject causes a lowering and flattening of the subject's renal vein pressure profile, even though the subject's central venous pressure is elevated, e.g., as described with reference to FIG. 4B of WO 14/141284 to Schwammenthal, which is incorporated herein by reference.

Typically, due to the reduction in pressure in the renal vein that is caused by the pumping of blood by blood-pump catheter 20, perfusion of the kidney increases. In turn, this may cause pressure in the renal veins to rise relative to the pressure in the renal veins immediately subsequent to initiation of the pumping, due to increased blood flow into the renal vein. Typically, even after perfusion of the kidney increases, the pump is configured to maintain the pressure in the renal vein at a lower value than the pressure in the renal vein before the initiation of the pumping. For some applications, in addition to lowering the subject's renal vein pressure, and/or increasing perfusion of the subject's kidney, blood-pump catheter 20 performs ultrafiltration on the subject's blood.

It is noted that, for some applications, due to the reduction in pressure in the renal vein that is caused by the pumping of blood by blood-pump catheter 20, the subject's renal vascular resistance decreases, in accordance with physiological mechanisms that are described, for example, in an article by Haddy et al., entitled "Effect of elevation of intraluminal pressure on renal vascular resistance" (Circulation Research, 1956), which is incorporated herein by reference. It is further noted that a treatment of the subject that increases renal perfusion by increasing blood pressure in the subject's renal arteries would typically not effect the aforementioned physiological mechanisms.

Typically, when blood-pump catheter 20 is used to reduce pressure in the subject's renal veins, it is expected that there will be an improved responsiveness by the subject to administration of diuretics to the subject, due to the reduction in renal venous pressure. Therefore, for some applications, a reduced dosage of diuretics may be administered to the subject relative to a dosage of diuretics that would be administered to the subject in the absence of performing the techniques described herein. Alternatively, a regular dosage of diuretics may be administered to the subject, but the diuretics may have a greater effect on the subject, due to the reduction in renal venous pressure.

Typically, high central venous pressure leads to a high level of blood pressure within the heart, which in turn leads to the release of atrial natriuretic peptide (ANP) and B-type natriuretic peptide (BNP) by the subject, both of which act as natural diuretics. For some applications, when blood-pump catheter 20 is used to reduce pressure in the subject's renal veins, there is expected to be an improved responsiveness by the subject to the release of the natural diuretics by the subject, due to the reduction in renal venous pressure. For some applications, since the subject's central venous pressure is not lowered by using blood-pump catheter 20, it is expected that the subject will continue to release atrial natriuretic peptide (ANP) and B-type natriuretic peptide (BNP), even while the subject's renal venous pressure is reduced by the use of the blood pumps. Thus, for some applications, using blood-pump catheter 20 may result in the subject continuing to release atrial natriuretic peptide (ANP) and B-type natriuretic peptide (BNP), as well as resulting in the effectiveness of the aforementioned natural diuretics being greater than the effectiveness of the diuretics in the absence of the use of blood-pump catheter 20.

Typically, each of upstream and downstream pumps 24U and 24D includes an impeller 28, for example, any one of the impellers described in WO 14/141284 to Schwammenthal, which is incorporated herein by reference. In accordance with respective applications, impeller 28 may have a single blade, two blades (e.g., as described in WO 14/141284 to Schwammenthal, which is incorporated herein by reference), three blades (e.g., as described in WO 14/141284 to Schwammenthal, which is incorporated herein by reference), or more than three blades. For some applications, one or both of blood pumps 24U and 24D includes more than one impeller. Typically, ceteris paribus, by using more than one impeller in at least one of the pumps, in order to generate a given flow of blood with the pump, the force that impacts each of the impellers within the pump is smaller than if a single impeller were to be used in the pump.

For some applications, one or both of the pumps includes radially-expandable cage 30. Typically, cage 30 is configured to hold open the inner wall of the vena cava and to separate the inner wall of the vena cava from the impeller, such that the vena cava does not become injured by the impeller. As described hereinabove, typically, impeller 28 and 30 are shape set such as to assume radially-expanded configurations thereof in the absence of any radially-constraining force acting upon the impeller and/or the cage. Further typically, an engagement mechanism engages the impeller and the cage with respect to one another, such that in response to the cage becoming radially constrained the impeller becomes radially constrained, e.g., in accordance with apparatus and methods described in described in WO 14/141284 to Schwammenthal, which is incorporated herein by reference.

Figure 1C:
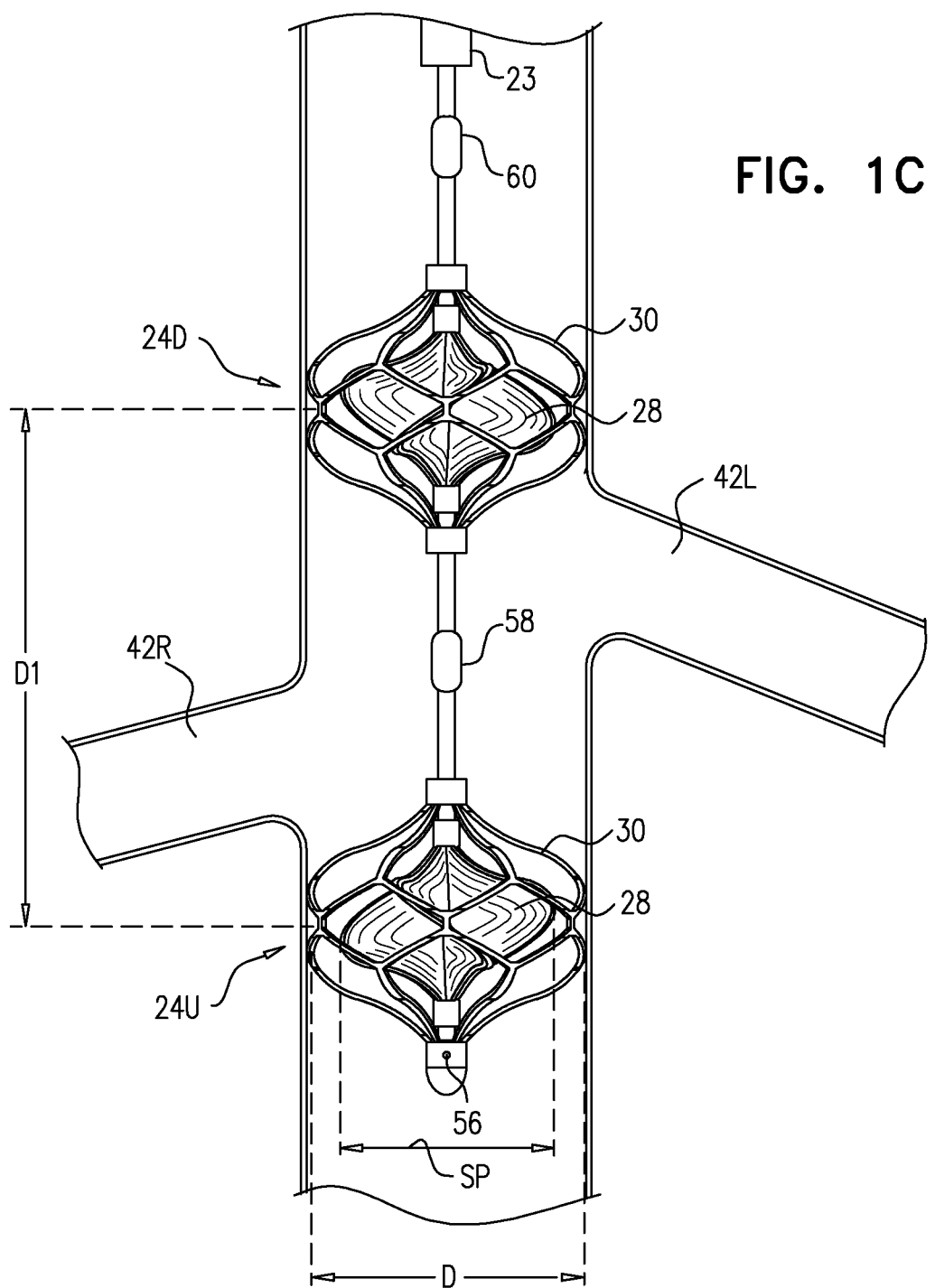

Referring now to FIG. 1C, typically, when blood-pump catheter 20 is placed inside vena cava 22, impeller 28 and cage 30 are substantially not radially constrained, due to the relatively low radial force exerted by the vena cava wall on the cage. Typically, a span SP of impeller 28, when the impeller is in a non-constrained configuration thereof inside the vena cava is more than 14 mm (e.g., more than 16 mm), and/or less than 28 mm (e.g., less than 22 mm), e.g., 14-28 mm, or 16-22 mm Typically, a diameter D of cage 30, when the cage is in a non-constrained configuration thereof inside the vena cava is more than 14 mm (e.g., more than 16 mm), and/or less than 40 mm (e.g., less than 35 mm), e.g., 14-40 mm, or 16-35 mm. Further typically, when blood-pump catheter 20 is used to enhance blood flow from the renal veins into the subject's vena cava, as described herein, a longitudinal distance D1 between centers of the impellers of the upstream and downstream pumps, measured along the longitudinal axis of the catheter, is typically more than 3 cm (e.g., more than 6 cm), and/or less than 18 cm (e.g., less than 14 cm), e.g., 3-18 cm, or 6-14 m.

Typically, impellers of pumps 24U and 24D are coupled to one or more motors 46 (FIG. 1A), which impart rotational motion to the impellers, via one or more shafts, the shaft(s) being housed inside blood-pump catheter 20. In accordance with respective applications, the motors are disposed outside of the subject's body (as shown), or are placed inside the subject's body (not shown).

For some applications, in order for the impellers to pump blood in opposite directions (i.e., in order for the upstream impeller to pump blood upstream, and the downstream pump to pump blood downstream), the impellers are rotated in opposite directions from one another, as viewed from an external reference point.

Figure 1D:
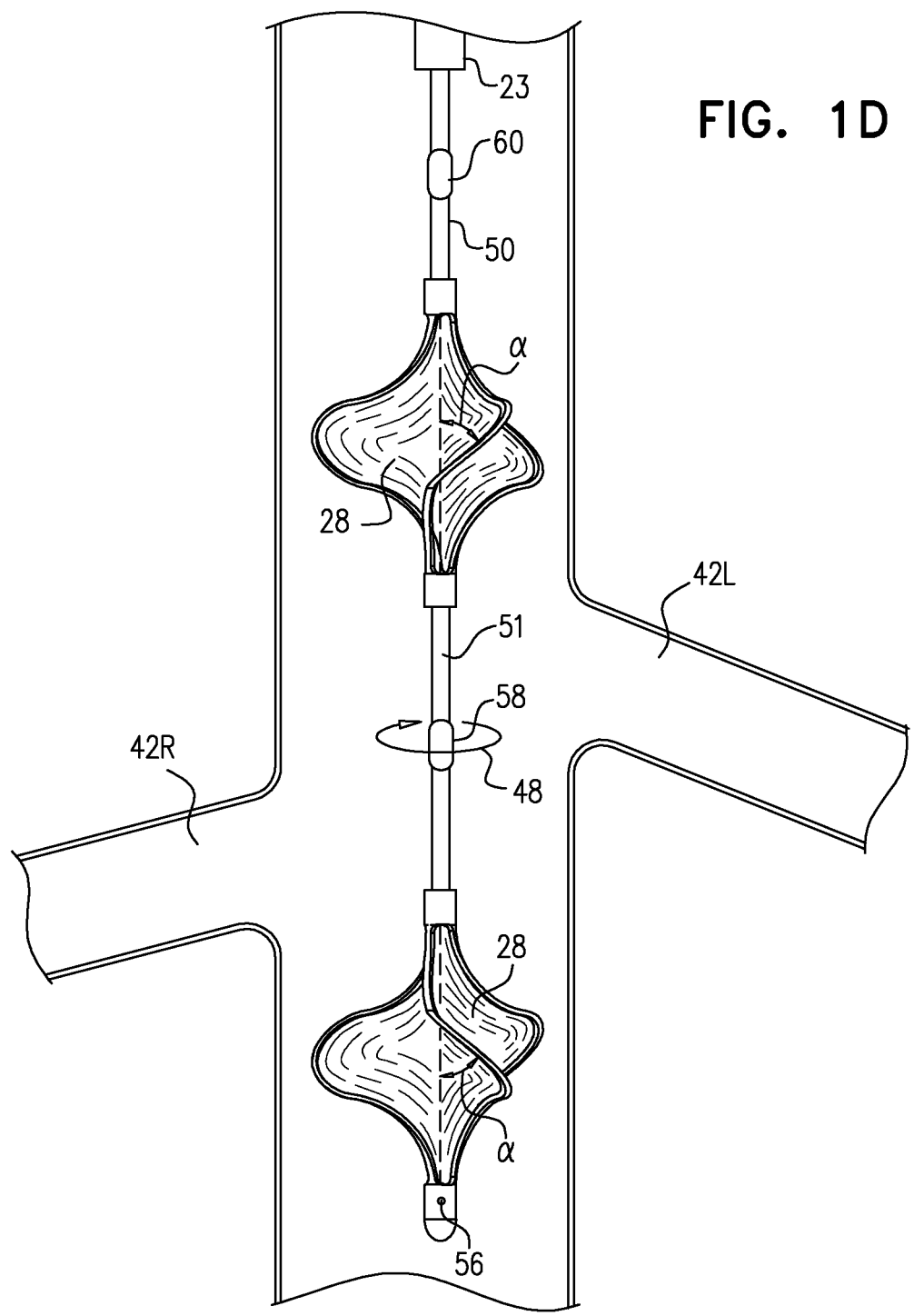

Referring now to FIG. 1D, typically, impellers 28 of upstream and downstream pumps 24U and 24D are rotated in the same rotational direction as one another, as viewed from an external reference point (e.g., in the direction of arrow 48 (i.e., clockwise), or counterclockwise), but the impellers are disposed on the catheter such that the rotation of the impellers in this direction of rotation causes the impellers to pump blood in respective, opposite directions. It is noted that the rotational direction of the impellers "as viewed from an external reference point" should be interpreted to mean the direction of rotational motion of the impellers as observed from any point that is not undergoing the same rotational motion as either of the impellers. (For illustrative purposes, FIG. 1D shows the impellers in the absence of the cages, although typically, the impellers are used together with cages, as described hereinabove.)

Typically, for such applications, a single motor is used to rotate both of the impellers. A shaft 50 is used to impart the rotational motion from the motor to the proximal impeller. An additional shaft 51, which is in series with shaft 50, couples the proximal impeller to the distal impeller and imparts the rotational motion from the proximal impeller to the distal impeller. For some applications, by using a single series of shafts to impart rotation to impellers 28 of both upstream and downstream pumps 24U and 24D, the diameter of blood-pump catheter 20 is reduced relative to if parallel shafts were used, in order to impart rotation to the upstream and downstream impellers.

For some applications, the angles and/or orientations of the impeller blades of impellers 28 of upstream and downstream pumps 24U and 24D may be such as to cause the impellers to pump blood in respective, opposite directions. For some applications, as shown in FIG. 1D, each propeller is shaped and/or oriented in the mirror image of the other, the axis of reflection being orthogonal to the longitudinal axes of the impellers. Typically, the upstream and downstream impellers are of opposing-handedness to one another, a first one of the impellers being a left-handed impeller, and the other one of the impellers being a right-handed impeller. It is generally the case that impellers of opposing handedness that are positioned parallel to one another, facing the same direction as one another, and rotating in opposite rotational directions from one another, generate flow in the same direction as one another. In accordance with the present invention, the upstream and downstream impellers are typically disposed upon shaft 51 such that the impellers are facing in opposite directions to one another. As described hereinabove, the impellers are typically rotated in the same rotational direction as one another, as viewed from an external reference point. The result of the impellers (a) being of opposing handedness to one another, and (b) facing in opposite directions, is that, when the impellers are rotated in the same direction as one another about an axis defined by shaft 51, the impellers pump blood in opposite directions from one another.

Typically, the blades of the downstream impeller are oriented such that, as the downstream impeller rotates in the direction of arrow 48, the downstream impeller pumps in the downstream direction. The blades of the upstream impeller are oriented such that, as the upstream impeller rotates in the direction of arrow 48, the upstream impeller pumps in the upstream direction.

As described in further detail hereinbelow, for some applications, upstream and downstream pumps 24U and 24D and blood-pump catheter 20 are placed within a main artery upstream and downstream of bifurcations of the artery with one or more branching arterial systems that branch from the main artery and supply a given organ, mutatis mutandis. For such applications, the blades of the downstream impeller are oriented such that, as the downstream impeller is rotated, the downstream impeller pumps in the upstream direction (toward the bifurcations). The blades of the upstream impeller are oriented such that, as the upstream impeller rotates is rotated, the upstream impeller pumps in the downstream direction (toward the bifurcations), such that blood flow into the branching arterial system is increased, thereby increasing perfusion of the organ.

For some applications, the blades of the impellers of the upstream and downstream pumps are configured to pump blood in the same direction as one another (e.g., in the antegrade direction). For example, the impellers may be of the same handedness as one another, placed upon catheter 20 such that the impellers are facing in the same direction as one another, and rotated in the same direction as one another, as viewed from an external reference point. Alternatively, the two impellers may be of opposing handedness to one another, placed within the vena cava such that the two impellers are facing in the same direction as one another, and rotated in opposite directions to one another, as viewed from an external reference point.

For some applications, blades of the upstream and downstream impellers are disposed at an angle alpha with respect to the longitudinal axes of the impellers, the blades of the respective impellers being oriented in opposite directions. For some applications, angle alpha is greater than 15 degrees (e.g., greater than 25 degrees), and/or less than 45 degrees (e.g., less than 35 degrees), e.g. 15-45 degrees, or 25-35 degrees.

For some applications, impellers 28 of upstream and downstream pumps 24U and 24D are rotated at respective rotation rates, in order to cause the pumping of blood in the upstream and downstream directions to be performed at respective rates. Alternatively, the impellers are rotated at the same rotation rate (and, typically, in the same direction), but the impellers are sized, shaped, and/or oriented such that the rate at which blood is pumped, respectively, in the upstream and downstream directions, by the respective impellers, is not equal.

Typically, a control unit 52 and a user interface 54 are disposed outside the subject's body. Further typically, the control unit receives inputs from one or more pressure sensors 56, 58, and/or 60, e.g., as shown in FIGS. 1A-D.

In accordance with some applications:

(a) a pressure sensor 56 is disposed on the upstream side of upstream blood pump 24U and is configured to measure pressure within the vena cava upstream of the low-pressure region of the vena cava, which is typically indicative of venous pressure within the subject's lower body;

(b) a pressure sensor 58 disposed between the two blood pumps, and is configured to measure pressure within the low-pressure region of the vena cava between the two blood pumps, which is typically indicative of blood pressure within the subject's renal veins; and/or (c) a pressure sensor 60 is disposed on the downstream side of downstream blood pump 24D and is configured to measure pressure within the vena cava downstream of the low-pressure region of the vena cava, which is typically indicative of the subject's central venous pressure close the subject's right heart.

For some applications, blood-pump catheter 20 includes pressure sensor 58 disposed between the two blood pumps, and is configured to measure pressure within the low-pressure region of the vena cava between the two blood pumps, which is typically indicative of blood pressure within the subject's renal veins, and the blood-pump catheter does not include pressure sensor 56, or pressure sensor 60.

For some applications, control unit 52 controls pumps 24U and 24D, e.g., by controlling rotation of impellers 28, responsively to one or more of the above-described inputs. Typically, user interface 54 displays the subject's current lower-body venous pressure, renal venous pressure, and/or central venous pressure, based upon the signals generated by sensors 56, 58, and/or 60. Typically, based upon the current values of the subject's lower-body venous pressure, renal venous pressure, and/or central venous pressure, a user (such as a healthcare professional) inputs a target value for the subject renal venous pressure, via the user interface. In response thereto, control unit 52 controls the speed of the rotation of the impellers, such that the impellers pump blood away from the renal veins at a flow rate that is such as to reduce the renal venous pressure toward the target level, as indicated by the user. For some applications, in response a signal received from sensor 60 indicating that the central venous pressure is at the target renal venous pressure, the control unit stops the impellers rotating. For some applications, the control unit receives an input from an additional sensor (such as a flow sensor and/or an oxygen-saturation sensor, and/or a thermal flow sensor, e.g., as described with reference to FIGS. 22Ai-22Cii of WO 14/141284 to Schwammenthal, which is incorporated herein by reference), and the control unit controls the speed of the rotation of the impellers responsively to an input from the additional sensor.

It is noted that control unit 52 typically includes a computer processor that comprises circuitry and that is configured to execute the actions described herein. Typically, the operations described herein that are performed by the computer processor transform the physical state of a memory, which is a real physical article that is in communication with the computer processor, to have a different magnetic polarity, electrical charge, or the like depending on the technology of the memory that is used. Control unit 52 is typically a hardware device programmed with computer program instructions to produce a special purpose computer. For example, when programmed to perform the techniques described herein, control unit 52 typically acts as a special purpose renal-venous-pressure-modulating computer processor.

It is further noted that user interface 54 typically includes any type of user interface configured to receive inputs from a user and/or to provide outputs to the user. For example, the user interface may include one or more input devices (such as a keyboard, a mouse, a trackball, a joystick, a touchscreen monitor, a touchpad, a voice-command interface, a smartphone, a tablet computer, and/or other types of input devices that are known in the art), and/or one or more output devices (such as a monitor, an audio output device, a smartphone, a tablet computer, and/or other types of output devices that are known in the art).

Figure 2:
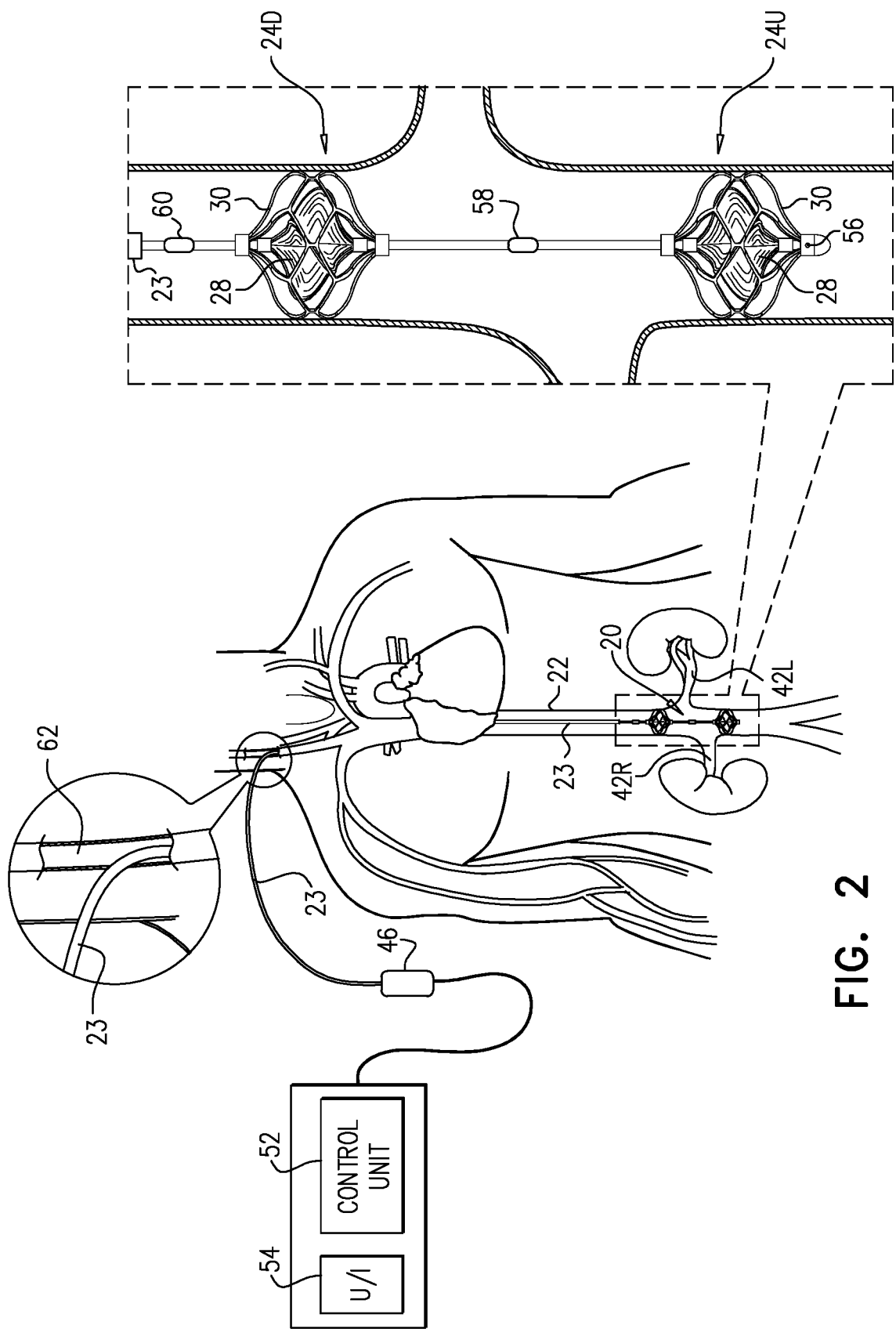
FIG. 2 is a schematic illustration of the catheter of FIGS. 1A-D inserted into the subject's vena cava via the subject's right jugular vein, in accordance with some applications of the present invention.

Reference is now made to FIG. 2, which is a schematic illustration of blood-pump catheter 20 being inserted into the subject's vena cava 22 via the subject's right jugular vein 62 (through guide catheter 23), in accordance with some applications of the present invention. For some applications, instead of being inserted via the subclavian vein (as shown in FIG. 1A, for example), blood-pump catheter 20 is inserted into the vena cava via the subject's right jugular vein, or via another vein that is above the subject's inferior vena cava. In all other aspects, blood-pump catheter 20 and the functioning thereof are generally as described with reference to FIGS. 1A-D.

Figure 3:
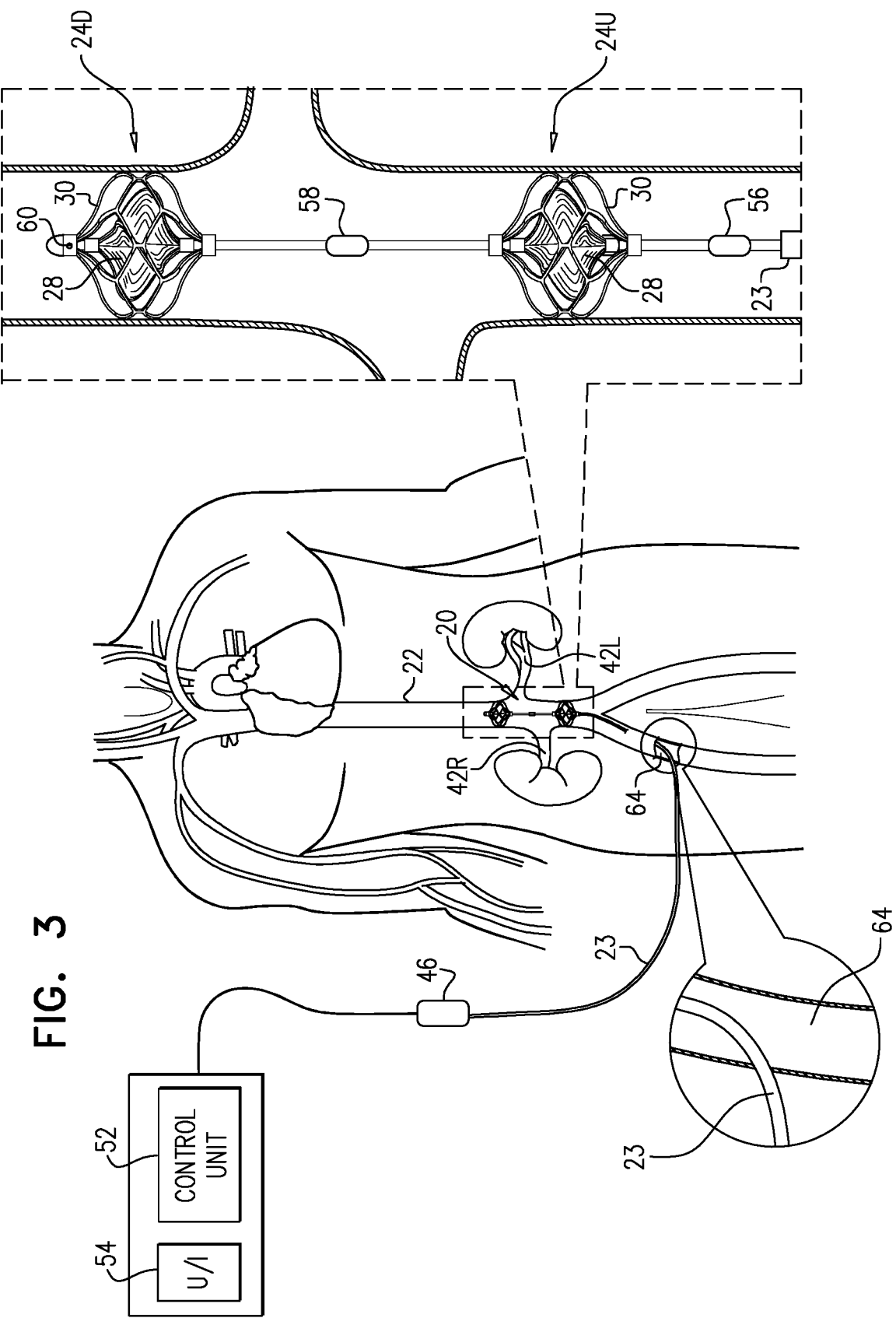
FIG. 3 is a schematic illustration of a blood-pump catheter inserted into a subject's vena cava via the subject's femoral vein, a downstream pump being disposed upon the catheter distally to an upstream pump, in accordance with some applications of the present invention.

Reference is now made to FIG. 3, which is a schematic illustration of blood-pump catheter 20 being inserted into the subject's vena cava 22 via the subject's femoral vein 64 (through guide catheter 23), downstream pump 24D being disposed upon the catheter distally to upstream pump 24U, in accordance with some applications of the present invention. For some applications, instead of being inserted via the subclavian vein (as shown in FIG. 1A, for example), blood-pump catheter 20 is inserted into the vena cava, via the subject's femoral vein 64, or via another vein that is below the subject's inferior vena cava. Typically, downstream blood pump 24D is disposed on blood-pump catheter 20 distally to upstream blood pump 24U. Blood-pump catheter 20 is configured to be placed within the vena cava, such that the upstream pump is disposed upstream of the junctions of the vena cava with all of the subject's renal veins 42, and such that the downstream pump is disposed downstream of the junctions of the vena cava with all of the subject's renal veins. Other than the dispositions of the upstream and downstream blood pumps with respect to blood-pump catheter 20, blood-pump catheter 20, as shown in FIG. 3, and the functioning thereof, is generally similar to that described with reference to blood-pump catheter 20 as shown in FIGS. 1A-D.

Figure 4:
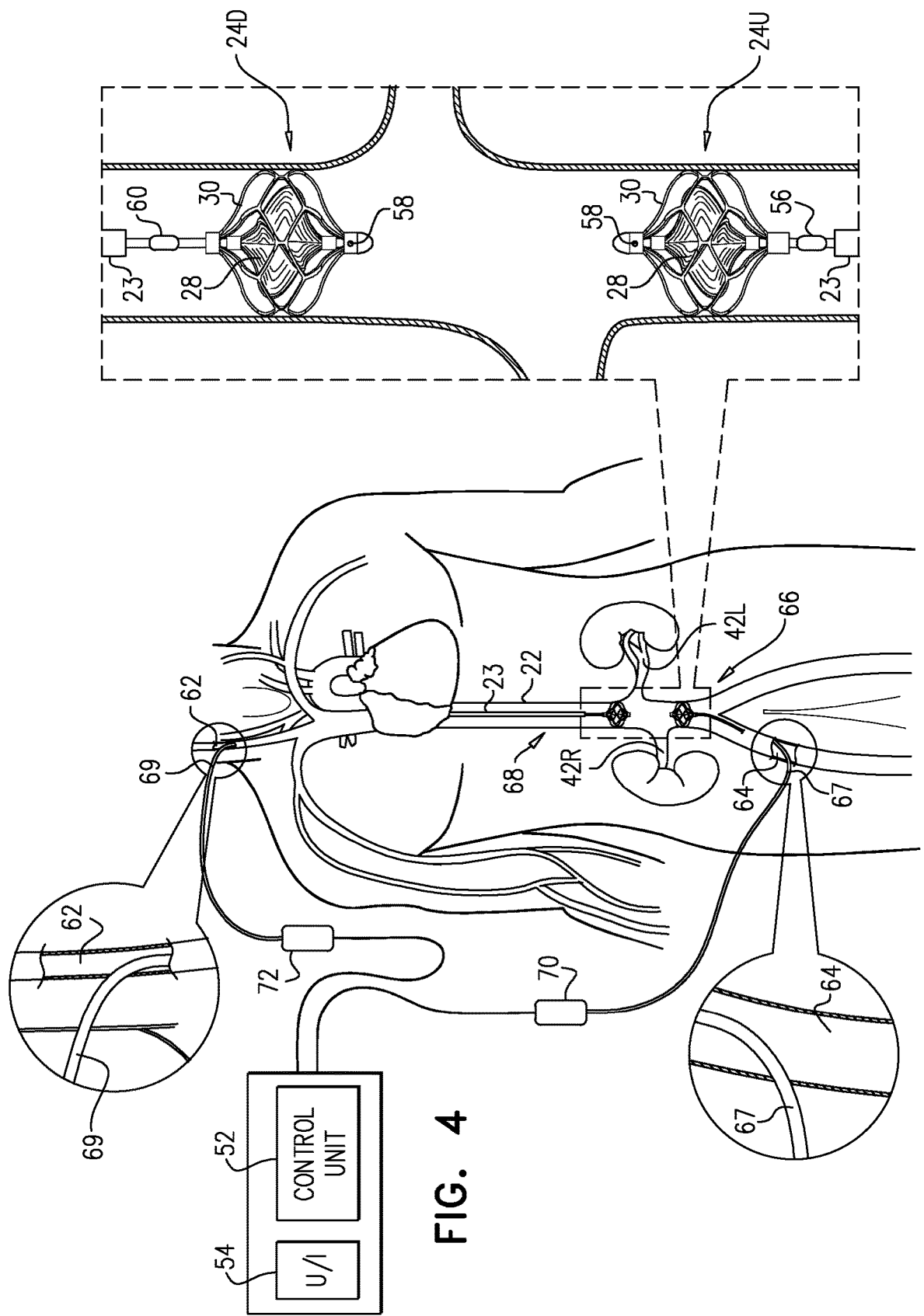
FIG. 4 is a schematic illustration of upstream and downstream pumps disposed on respective blood-pump catheters, in accordance with some applications of the present invention.

Reference is now made to FIG. 4, which is a schematic illustration of upstream and downstream pumps 24 U and 24D being disposed on respective catheters 66 and 68, in accordance with some applications of the present invention. For some applications, a first catheter 66 is inserted into vena cava 22 through a guide catheter 67 that is inserted via the subject's femoral vein 64, or via another vein that is below the subject's inferior vena cava. Upstream blood pump 24U is disposed on the first catheter, and is configured to be placed within the vena cava upstream of the junctions of the vena cava with all of the subject's renal veins, and to pump blood through the vena cava in the manner described hereinabove. A second catheter 68 is inserted into the vena cava through a guide catheter 69 that is inserted via the subject's jugular vein 62 (as shown), via the subclavian vein (not shown), or via a different vein that is above the subject's inferior vena cava. Downstream blood pump 24D is disposed on the second catheter, and is configured to be placed within the vena cava downstream of the junctions of the vena cava with all of the subject's renal veins, and to pump blood through the vena cava in the manner described hereinabove.

For applications in which the upstream and downstream blood pumps include impellers, typically, respective motors 70 and 72 are used to control rotation of the impellers. Further typically, control unit 52 controls both pumps (e.g., by controlling the rates of rotation of the impellers). For some applications, pressure sensors 56, 58 and 60 are disposed upon the first and/or second catheters, and are configured to detect indications of, respectively, lower body venous pressure, renal venous pressure, and central venous pressure. The control unit is configured to control the operation of the upstream and downstream pumps responsively to the detected indications, in accordance with the techniques described hereinabove.

Figure 5B:
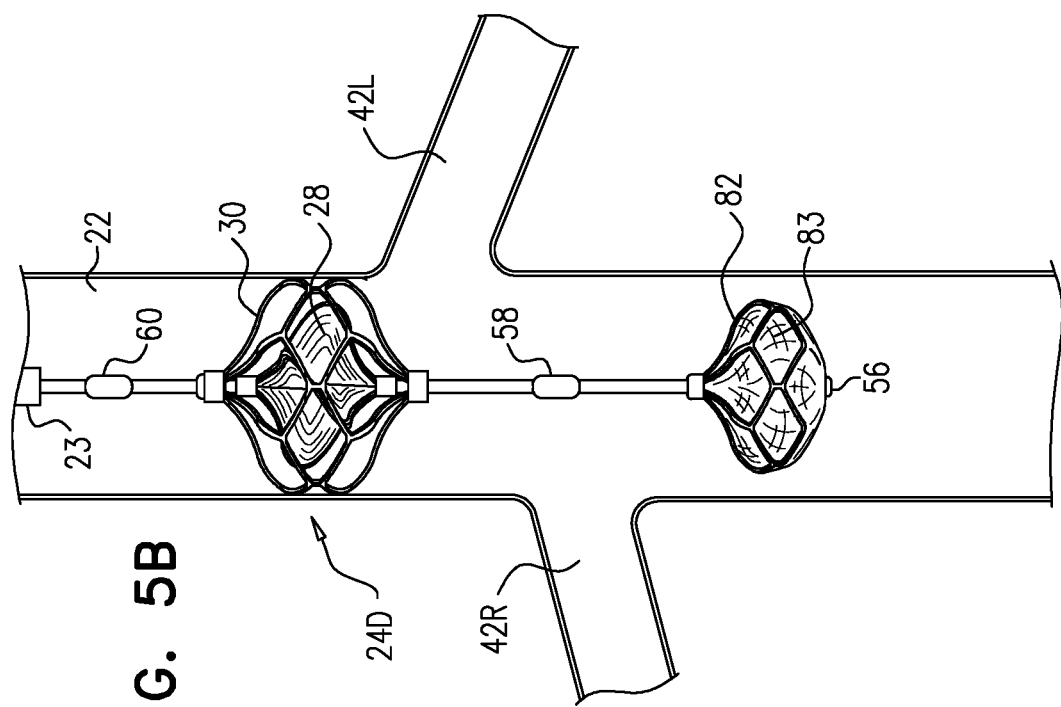
FIGS. 5A-5B are schematic illustrations of a catheter that includes a downstream pump and an occlusion element, such as a balloon (FIG. 5A), or a covered frame (FIG. 5B), in accordance with some applications of the present invention.
Figure 5A:
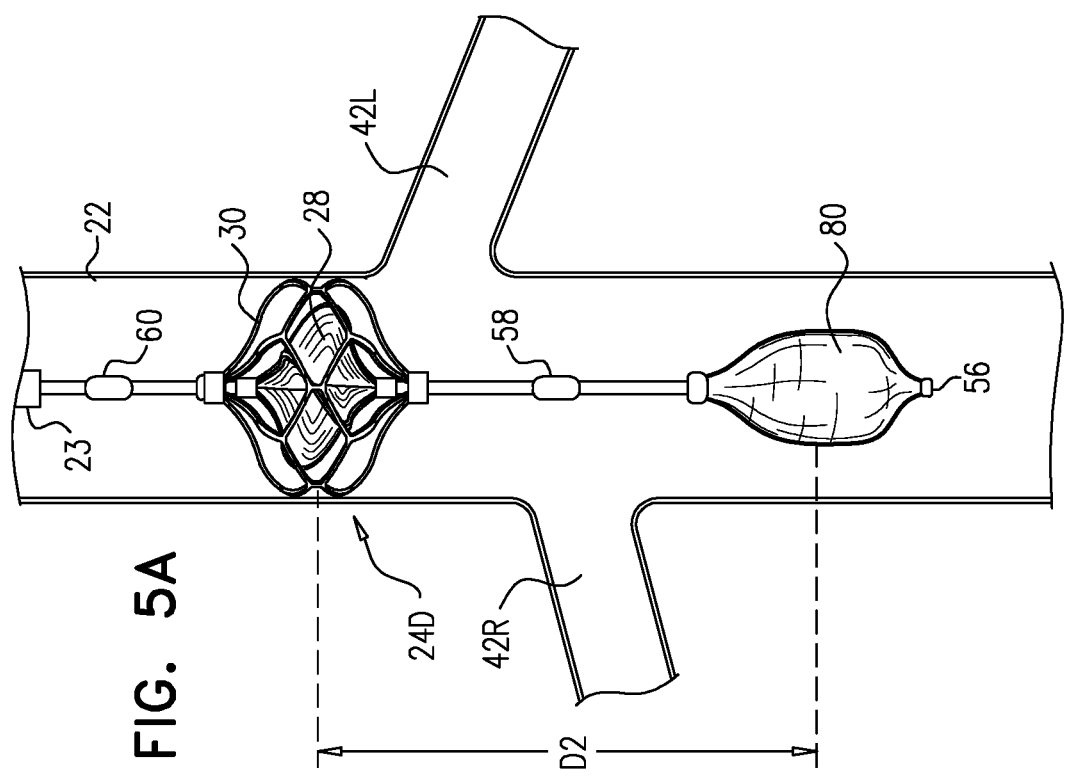

Reference is now made to FIGS. 5A-B, which are schematic illustrations of blood-pump catheter 20, the catheter including downstream pump 24D and an occlusion element, such as a balloon 80 (FIG. 5A), or a covered frame 82 (FIG. 5B), in accordance with some applications of the present invention. For some applications, downstream pump is placed inside vena cava 22, downstream of the junctions of the vena cava with all of the subject's renal veins. The downstream pump pumps blood through the vena cava, in the downstream direction, away from the junctions of the vena cava with the renal veins, in the manner described hereinabove. As an alternative to, or in addition to using an upstream pump as described hereinabove, the occlusion element is placed inside the vena cava upstream of the junctions of the vena cava with the subject's renal veins. Typically, the occlusion element is configured to partially occlude the subject's vena cava upstream of the junctions of the vena cava with the subject's renal veins. The occlusion element is configured to partially occlude the subject's vena cava such that, in response to the pumping of the downstream blood pump, there is not a substantial increase of blood flow from the subject's lower body toward the subject heart, but such that a region of low pressure within the vena cava is generated, between the occlusion element and the downstream blood pump, within which the blood pressure is lower than the subject's central venous pressure. Typically, by generating a region of low pressure, blood flow from the renal veins into the vena cava increases, thereby lowering renal blood pressure and enhancing renal perfusion. It is noted that the occlusion element is configured to partially occlude, but not to totally occlude, the vena cava, in such a manner as to generate a region of low pressure within the vena cava, but to allow a substantial flow of blood through the vena cava When blood-pump catheter 20 is used to enhance blood flow from the renal veins into the subject's vena cava, as described herein, a longitudinal distance D2 between the longitudinal center of the impeller of the downstream pump and the longitudinal center of the occlusion element, measured along the longitudinal axis of the catheter, is typically more than 3 cm (e.g., more than 6 cm), and/or less than 18 cm (e.g., less than 14 cm), e.g., 3-18 cm, or 6-14 cm.

As used in the present application, including in the claims, a "longitudinal axis" of a structure is the set of all centroids of cross-sectional sections of the structure along the structure. Thus the cross-sectional sections are locally perpendicular to the longitudinal axis, which runs along the structure. (If the structure is circular in cross-section, the centroids correspond with the centers of the circular cross-sectional sections.) As used in the present application, including in the claims, the term "longitudinal center" denotes the center of a structure along the direction of the structure's longitudinal axis.

For some applications, the occlusion element is balloon 80, as shown in FIG. 5A. Alternatively or additionally, the occlusion element is covered frame 82, as shown in FIG. 5B. For example, the frame may be a rigid frame made of a shape-memory element (such as nitinol) that is covered with a blood-impermeable material 83 (e.g., polyester, polyurethane, and/or a different polymer).

As described hereinabove, typically, the occlusion element is configured to partially occlude the vena cava upstream of the junctions of the vena cava with the subject's renal veins. For some applications, the diameter to which the occlusion element is expanded is controllable. For example, inflation of the balloon may be controllable, or the stent may be expandable (e.g., by heating the stent, or by applying an electrical current to the stent). For some applications, the extent to which the occlusion element occludes the vena cava is controlled by a control unit (e.g., control unit 52) responsively to the blood pressure detected by blood pressure sensor 56, 58, and/or 60, in response to an input from a different sensor (such as a flow sensor and/or an oxygen-saturation sensor, and/or a thermal flow sensor, e.g., as described with reference to FIGS. 22Ai-Cii of WO 14/141284 to Schwammenthal, which is incorporated herein by reference), and/or in response to an input from a user. For some applications, the rate at which pump 24D pumps blood away from the renal veins (e.g., the rate at which impeller 28 of the pump is rotated), as well as the extent to which the occlusion element occludes the vena cava is controlled by a control unit responsively to the blood pressure detected by blood pressure sensor 56, 58, and/or 60, in response to an input from a different sensor (such as a flow sensor and/or an oxygen-saturation sensor, and/or a thermal flow sensor, e.g., as described with reference to FIGS. 22Ai-Cii of WO 14/141284 to Schwammenthal, which is incorporated herein by reference), and/or in response to an input from a user.

Although FIGS. 5A and 5B show the downstream blood pump and the occlusion element disposed on a catheter that is inserted into the vena cava from above the junctions of the vena cava with the subject's renal veins (e.g., via the subject's subclavian vein or jugular vein), for some applications, the downstream blood pump and the occlusion element are disposed on a catheter that is inserted into the vena cava from below the junctions of the vena cava with the subject's renal veins (e.g., via the subject's femoral vein), mutatis mutandis. Alternatively or additionally, the occlusion element is disposed on a first catheter which is inserted into the vena cava from below the junctions of the vena cava with the subject's renal veins (e.g., via the subject's femoral vein), and the downstream blood pump is disposed on a second catheter, which inserted into the vena cava from above the junctions of the vena cava with the subject's renal veins (e.g., via the subject's subclavian vein, or jugular vein).

Figure 6:
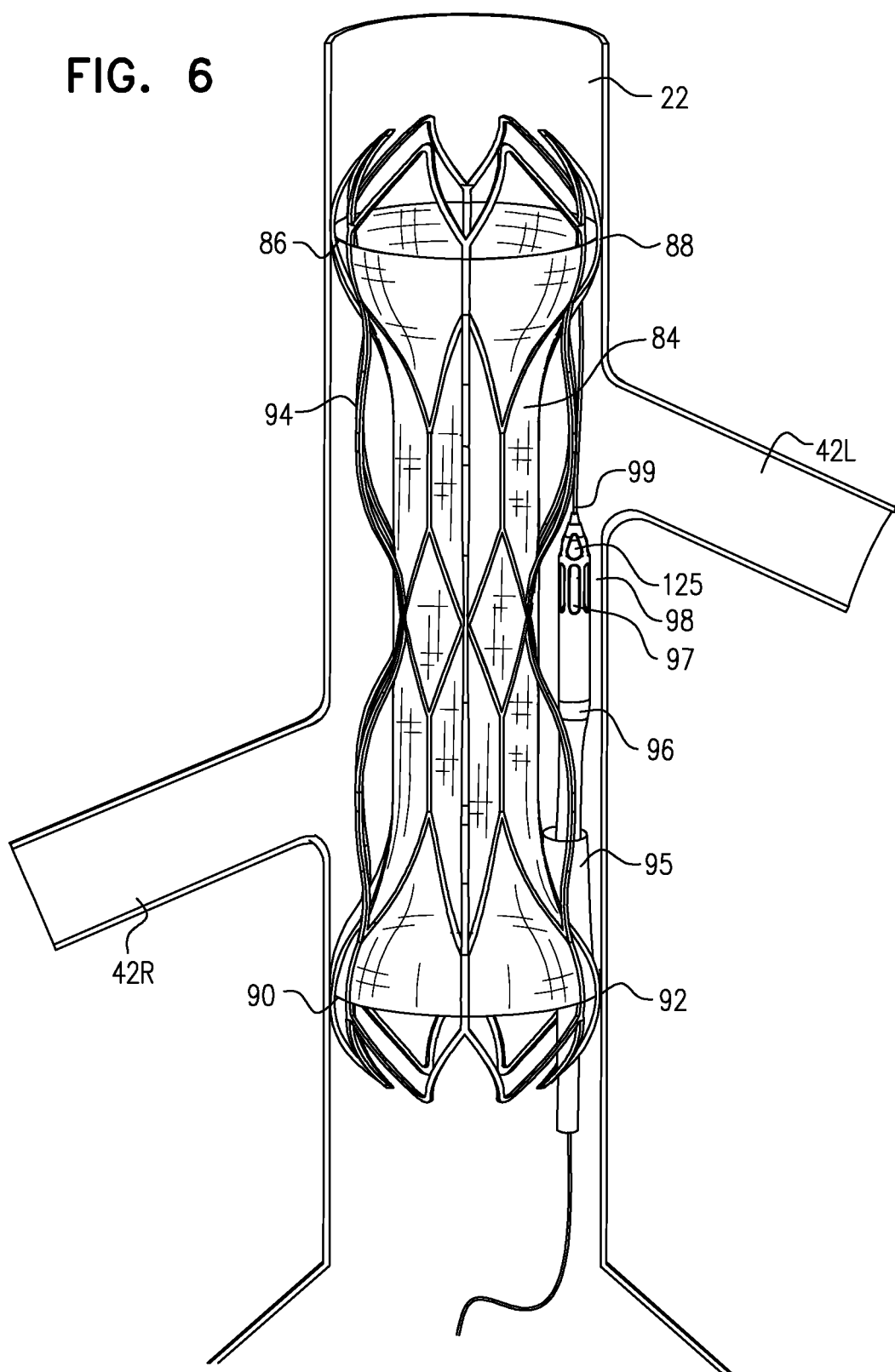
FIG. 6 is a schematic illustration of a blood-impermeable sleeve configured to occlude blood flow from a subject's vena cava to the subject's renal veins, as described in WO 14/141284, which is incorporated herein by reference, and in accordance with some applications of the present invention.

Reference is now made to FIG. 6, which is a schematic illustration of a blood-impermeable sleeve 84 configured to occlude blood flow from a subject's vena cava to the subject's renal veins, as described in WO 14/141284, which is incorporated herein by reference. Typically, the sleeve is placed within the vena cava such that a downstream end 86 of the sleeve is coupled to the wall of the vena cava at a first location 88 that is downstream of all renal veins 42 of the subject (e.g., left and right renal vein in a typical subject that has two renal veins), and such that an upstream end 90 of the sleeve is coupled to a wall of the vena cava at a second location 92 that is upstream of all renal veins of the subject. Thus, the sleeve isolates the blood in the renal veins into a compartment that is separated from blood flow through the center of the vena cava. Typically, a rigid structure, e.g., a stent 94 as shown, is configured to couple the upstream and downstream ends of the sleeve to the vena cava.

A pump 96 is configured to pump blood through inlet holes 97, from a location that is exterior to sleeve 98 (i.e., from the isolated compartment) to a location that is in fluid communication with the interior of the sleeve (e.g., a location within the vena cava upstream or downstream of the sleeve). Thus, the pump pumps blood out of the subject's renal veins and into the subject's vena cava. The sleeve prevents backflow of blood from the vena cava into the renal veins.

For some applications, sleeve 84 and stent 94 are inserted into the subject's vena cava, while a guidewire 99 is disposed inside a pump-accommodating sleeve 95. Subsequent to anchoring sleeve 84 and stent 94 to the vena cava, pump 96 is inserted through the pump-accommodating sleeve, by advancing the pump over the guidewire.

Sleeve 84 and pump 96 are generally as described with reference to FIGS. 10A-D of WO 14/141284 to Schwammenthal, which is incorporated herein by reference.

It is noted that the effect of inserting sleeve 84 into the vena cava and activating pump 96 in the described manner is that a low-pressure region is generated within the subject's vena cava, adjacent to junctions of the vena cava with the subject's renal veins, blood pressure within the low-pressure region being lower than central venous pressure of the subject. Similarly, by using blood-pump catheter 20 as described with reference to FIGS. 1A-5B, a low-pressure region is generated within the subject's vena cava, adjacent to junctions of the vena cava with the subject's renal veins, blood pressure within the low-pressure region being lower than central venous pressure of the subject. The effect of generating the low-pressure region within the vena cava is typically that blood flow from the renal veins to the vena cava is increased, thereby reducing renal venous pressure, and increasing renal perfusion.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

In general, in the specification and in the claims of the present application, the term "downstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is downstream, with respect to the direction of antegrade blood flow through the blood vessel, relative to a different location within the blood vessel. The term "upstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is upstream with respect to the direction of antegrade blood flow through the blood vessel, relative to a different location within the blood vessel.

It is noted that blood pumps 24U and 24D, the catheters upon which the blood pumps are disposed (e.g., blood-pump catheter 20, catheter 66, and catheter 68), and the occlusion elements described with reference to FIGS. 5A-B, and other devices described herein, are generally described as being placed within the subject's vena cava, such that the upstream pump or the occlusion element is disposed upstream of junctions of the vena cava with the subject's renal veins, and the downstream pump is disposed downstream of the junctions of the vena cava with the subject's renal veins. However, it is noted that the scope of the present invention includes placing upstream pump 24U or the occlusion element in any main vein upstream of a tributary venous system, and placing downstream pump 24D downstream of said tributary venous system, and configuring the pump(s) (e.g., via the direction of rotation of impellers of the pumps, or the orientation of the pumps) to generate preferential flow from the tributaries into the main vein, mutatis mutandis. For example, the pump(s) could be used to generate flow from the subject's hepatic veins into the subject's vena cava, in order to increase perfusion of the subject's liver, mutatis mutandis. For some applications, the upstream pump or the occlusion element is placed within a main vein upstream of two or more tributary venous systems into the main vein (e.g., within the vena cava upstream of the renal venous system and the hepatic venous system). The downstream pump is placed downstream of the two or more tributary venous systems. The pump(s) are configured to generate preferential flow from both of the tributary venous systems into the main vein by pumping blood through the main vein, in the manner described herein.

For such applications, upstream pump 24U or the occlusion element is placed in a main vein upstream of a tributary venous system, and downstream pump 24D is placed downstream of said tributary venous system, and the pump(s) are configured (e.g., via the direction of rotation of impellers of the pumps, or the orientation of the pumps) to reduce flow from the tributaries into the main vein. For some such applications, the blades of the downstream impeller are oriented such that, as the downstream impeller is rotated, the downstream impeller pumps in the upstream direction (toward the junction between the tributary system and the main vein). The blades of the upstream impeller are oriented such that, as the upstream impeller rotates is rotated, the upstream impeller pumps in the downstream direction (toward the junction between the tributary system and the main vein).

For some applications, the upstream and downstream pumps 24U and 24D, the catheter(s) upon which the blood pumps are disposed (e.g., blood-pump catheter 20, catheter 66, and catheter 68), and/or the occlusion elements described with reference to FIGS. 5A-B, and other devices described herein, are placed within a main artery upstream and downstream of bifurcations of the artery with one or more branching arterial systems that branch from the main artery and supply a given organ, mutatis mutandis. For such applications, the upstream pump is typically configured to pump in the downstream direction (toward the bifurcations) and the downstream pump is configured to pump in the upstream direction (toward the bifurcations), such that blood flow into the branching arterial system is increased, thereby increasing perfusion of the organ. Alternatively or additionally, the occlusion element is placed downstream of the bifurcations of the artery with the one or more arterial systems and is configured to partially occlude the artery downstream of the bifurcations. For example, the upstream pump may be placed in the subject's aorta upstream of the subject's renal arteries and the downstream pump may be placed in the subject's aorta downstream of the subject's renal arteries, the pumps acting to pump blood into the renal arteries and toward the subject's kidneys. For some applications, upstream and downstream pumps, and/or occlusion elements are placed on both the arterial and venous sides of the subject's body in order to increase perfusion of a given organ or set of organs, in the manner described herein.

Although some applications of the present invention are described with reference to blood pumps 24D and 24U, according to which the blood pumps include impellers, the scope of the present invention includes using any other type of pump for pumping blood in the manner described herein, mutatis mutandis. For example, a roller pump, an Archimedes screw pump, a centrifugal pump, a pneumatic pump, and/or a compression pump may be used.

The scope of the present invention includes combining any of the apparatus and methods described herein with any of the apparatus and methods described in one or more of the following applications, all of which are incorporated herein by reference:

International Patent Application PCT/IL2014/050289 to Schwammenthal (published as WO 14/141284), filed Mar. 13, 2014, entitled "Renal pump," which claims priority from (a) US Provisional Patent Application 61/779,803 to Schwammenthal, filed Mar. 13, 2013, entitled "Renal pump," and (b) US Provisional Patent Application 61/914,475 to Schwammenthal, filed Dec. 11, 2013, entitled "Renal pump;" and International Patent Application PCT/IL2013/050495 to Tuval (published as WO 13/183060), filed Jun. 6, 2013, entitled "Prosthetic renal valve," which claims priority from US Provisional Patent Application 61/656,244 to Tuval, filed Jun. 6, 2012, entitled "Prosthetic renal valve."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
 placing a blood pump inside a body of a subject, the blood pump including:
  a motor disposed outside the body of the subject;
  a catheter;
  a first impeller disposed on the catheter;
  a second impeller disposed on the catheter, proximally to the first impeller,
  a series of one or more shafts extending from the motor to the first impeller and from the first impeller to the second impeller;
  wherein the blood pump has one or more characteristics selected from the group consisting of: (a) the first and second impellers are shaped differently from each other, when the first and second impellers are in non-radially-constrained configurations, and (b) the first and second impellers are sized differently from each other, when the first and second impellers are in non-radially-constrained configurations; and
 pumping blood within the subject's body, by driving the first and second impellers to rotate when the first and second impellers are in non-radially-constrained configurations, by the motor imparting rotational motion to the first and second impellers via the one or more shafts.

2. The method according to claim 1, wherein, when the first and second impellers are in non-radially-constrained configurations, the first and second impellers are of opposing handedness with respect to one another, with one of the impellers being a left-handed impeller, and the other one of the impellers being a right-handed impeller.

3. The method according to claim 1, wherein driving the first and second impellers to rotate comprises driving the first and second impellers to rotate at the same rotation rate as each other, and wherein, when the first and second impellers are in non-radially-constrained configurations, the first and second impellers are sized differently from one another, such that, when the impellers are rotated at the same rotation rate as each other, flow rates at which blood is pumped by each of the impellers are different from each other.

4. The method according to claim 1, wherein driving the first and second impellers to rotate comprises driving the first and second impellers to rotate at the same rotation rate as each other, and wherein, when the first and second impellers are in non-radially-constrained configurations, the first and second impellers are shaped differently from one another, such that, when the impellers are rotated at the same rotation rate as each other, flow rates at which blood is pumped by each of the impellers are different from each other.

5. The method according to claim 1, wherein driving the first and second impellers to rotate comprises driving the first and second impellers to rotate at the same rotation rate as each other, and wherein, when the first and second impellers are in non-radially-constrained configurations, the first and second impellers are oriented differently from one another, such that, when the impellers are rotated at the same rotation rate as each other, flow rates at which blood is pumped by each of the impellers are different from each other.

6. The method according to claim 1, wherein driving the first and second impellers to rotate comprises driving the first and second impellers to rotate in the same direction as one another.

* * * * *